(12) United States Patent
Kubista et al.

(10) Patent No.: US 6,329,144 B1
(45) Date of Patent: Dec. 11, 2001

(54) PROBE FOR ANALYSIS OF TARGET NUCLEIC ACIDS

(75) Inventors: Mikael Kubista, Molnlycke; Nicke Svanvik, Gothenburg, both of (SE)

(73) Assignee: Forskarpatent i Västsverige AB, Göteborg (SE)

( * ) Notice: Subject to any disclaimer, the term of this patent is extended or adjusted under 35 U.S.C. 154(b) by 0 days.

(21) Appl. No.: 09/194,679

(22) PCT Filed: May 30, 1997

(86) PCT No.: PCT/SE97/00953

§ 371 Date: Jan. 29, 1999

§ 102(e) Date: Jan. 29, 1999

(87) PCT Pub. No.: WO97/45539

PCT Pub. Date: Dec. 4, 1997

(30) Foreign Application Priority Data

May 31, 1996 (SE) .................................................. 9602183

(51) Int. Cl.⁷ .............................. C12Q 1/68; C07H 21/04
(52) U.S. Cl. ................................ 435/6; 436/94; 536/24.3
(58) Field of Search ................................ 435/6; 436/94; 536/24.3; 546/165, 256, 152, 176

(56) References Cited

U.S. PATENT DOCUMENTS

| | | | |
|---|---|---|---|
| 4,883,867 | 11/1989 | Lee et al. | 536/28 |
| 4,937,198 | * 6/1990 | Lee et al. | 436/94 |
| 5,268,486 | * 12/1993 | Waggoner et al. | 548/427 |
| 5,321,130 | 6/1994 | Yue et al. | 536/23.1 |
| 5,410,030 | 4/1995 | Yue et al. | 536/23.1 |
| 5,436,134 | 7/1995 | Haugland et al. | 435/34 |
| 5,453,505 | * 9/1995 | Lee et al. | 544/124 |
| 5,486,616 | * 1/1996 | Waggoner et al. | 548/217 |
| 5,569,587 | * 10/1996 | Waggoner | 435/6 |
| 5,569,766 | * 10/1996 | Waggoner et al. | 548/150 |
| 5,597,696 | * 1/1997 | Linn et al. | 435/6 |
| 5,627,027 | * 5/1997 | Waggoner | 435/6 |
| 5,658,751 | * 8/1997 | Yue et al. | 435/34 |

FOREIGN PATENT DOCUMENTS

| | | |
|---|---|---|
| 0492570A1 | 7/1992 | (EP) . |
| 0710668A2 | 5/1996 | (EP) . |
| 0714986A1 | 6/1996 | (EP) . |
| 92 20703 | 11/1992 | (WO) . |
| 94 24213 | 10/1994 | (WO) . |
| 96 11205 | 4/1996 | (WO) . |
| 96 13552 | 5/1996 | (WO) . |

OTHER PUBLICATIONS

Chemical Abstract vol. 94, 1981, p. 494.

* cited by examiner

Primary Examiner—Kenneth R. Horlick
(74) Attorney, Agent, or Firm—Birch Stewart Kolasch & Birch, LLP

(57) ABSTRACT

The invention is a probe for detecting nucleic acids having a particular sequence. It is composed of two joint units. One unit is chemically different from natural nucleic acids, but has the ability to recognize a particular sequence of bases or base pairs in single or double-stranded DNA of RNA. The other unit is a compound whose detectable properties are altered upon binding to nucleic acids.

51 Claims, 21 Drawing Sheets

A

B

C

I + II →

D

| Type of complex | Quantum yield | log(K) | $\varepsilon_{max}$ | abs. peak | Binding mode |
|---|---|---|---|---|---|
| | (at 25°C) | (at 100mM) | ($M^{-1} cm^{-1}$) | (nm) | |
| free TO | <1×10$^{-4}$ | - | 55000 | 500.6 | I |
| TO-ctDNA | 0.11 | 5.3 | 49500 | 509.4 | I |
| TO-poly(dA-dT)$_2$ | 0.07 | 5.5 | 60500 | 509.4 | I |
| TO-poly(dG-dC)$_2$ | 0.11 | 5.5 | 69200 | 510.6 | I |
| TO-poly(dA) | 0.09 | 4.8 | 52900 | 506.6 | I |
| TO-poly(dG) | 0.39 | 4.8 | - | - | I (II) |
| TO-poly(dC) | 0.009 | 3.4 | 37900 | 475.6 | II |
| TO-poly(dT) | 0.01 | 2.3 | 68000 | 476.0 | II |

A

B

C

PROBE FOR ANALYSIS OF TARGET NUCLEIC ACIDS

This application is the national phase under 35 U.S.C. §371 of prior PCT International Application No. PCT/SE97/00953 which has an international filing date of May 30, 1997 which designated the United States of America.

PROBE FOR ANALYSIS OF NUCLEIC ACIDS

The invention belongs to the category probes for hybridization to nucleic acids. Such probes are used in methods where specific genes, gene segments, RNA molecules and other nucleic acids are identified. These methods are primarily used clinically, for example to test tissue, blood and urine samples, in food technology, agriculture and in biological research.

BACKGROUND OF THE INVENTION

Probes for hybridization to nucleic acids (NA), with which we refer to both deoxyribonucleic acids (DNA) and ribonucleic acids (RNA), are used to demonstrate the presence of specific target sequences (TS) in complex mixtures. Traditional hybridization methods, as first described by Gillespie and Spiegelman (J. Mol. Biol. 12, 829, 1956), employ a probe based on an oligodeoxyribonucleotide equipped with a reporter group (RG) that usually is a radioisotope, and encompasses usually the following steps: the nucleic acid to be tested is immobilized on a paper, glass bead or plastic surface; an excess of probe complementary to the target sequence is added; the probe is allowed to hybridize; non-hybridized probe is removed; remaining probe bound to the immobilized target sequence is detected.

Non-hybridized probe is removed by extensive washing. This is usually the most time consuming and critical step in the procedure. Since the properties of non-hybridized and hybridized probe are not distinguishable, it is necessary that essentially all non-hybridized probe is removed. Since the hybridized probe is only attached through its interaction with the target sequence also some of it will be removed by washing, as well as some hybrids between TS and probe where TS was not sufficiently immobilized. Further, some probe may stick directly to the surface giving rise to a background signal. Finally, the requirement that non-hybridized probe must be removed makes in vivo and real time detection impossible.

A few methods to demonstrate hybridization without having to remove non-hybridized probe, so called homogeneous probing techniques, have been described.

Bannwarth et al., (Helvetica Chimica Acta, 71, 2085, 1988) have developed a method with probes composed of an oligodeoxyribonucleotide equipped with a ruthenium complex, where hybridization can be demonstrated from measurements of the probe fluorescence lifetime. Although the strategy is elegant, its application is limited to specialized laboratories that have sophisticated instrumentation, and can only be used by people with special training. Further, the ability of the method to distinguish hybridized and non-hybridized probe is not too good, particularly not in biological samples that may contain components that affect the probe fluorescence life time.

Barton J., (U.S. Pat. No. 5,157,032) describes a probe composed of a DNA-chain modified with a metal-ligand complex whose fluorescence intensity increases upon hybridization. These probes obtain only a modest fluorescence upon hybridization (a fluorescence quantum yield of 0.007, has been reported, Jenkins & Barton, J. Am. Chem. Soc., 114, 8736, 1992), which gives low sensitivity. Further, the probes are dicationic (charge +2), which leads to considerable non-specific contribution to the interaction and consequently a decreased ability to distinguish different sequences.

Yamana et al., (Nucl. & Nucl. 11 (2–4), 383, 1992) describe a probe composed of an oligonucleotide modified with pyrene, which under optimal conditions gives a 20-fold increase in fluorescence upon hybridization. The method has several disadvantages. Pyrene has complicated photophysics and its absorption and fluorescence properties depend on its closest surrounding; for example, it has a large tendency to form excimers (J. Michl & Erik W. Thulstrup in Spectroscopy with polarized light, $1^{st}$ Ed. VCH, 1986, ISBN 0-89573-346-3). Further, pyrene emits ultraviolet light (below 450 nm) that cannot be seen by the naked eye. Finally, pyrene is toxic (Yoshikawa et al., Vet. Hum. Toxicol. 29, 25, 1987).

Linn et al., (EP 0710 668 A2, U.S. Pat. No. 5,597,696) and Ishiguro et al., (Nucl. Acids Res. 24, 4992, 1996) describes probes composed of an oligonucleotide and an asymmetric cyanine dye. The fluorescence properties, such as fluorescence polarization, fluorescence lifetime and fluorescence intensity, of these probes are changed upon hybridization. These probes have several disadvantages and limitations. Measurements of fluorescence polarization and fluorescence lifetime require sophisticated and expensive instrumentation, and must be performed by people with specialist training. The change in fluorescence intensity is modest (a 4-fold increase under optimal conditions has been reported), making probing very sensitive to background, particularly at conditions that require excess of probe.

Heller et al., (EPA 070685) and Cardullo et al., (Proc. Natl. Acad. Sci. USA, 85, 8790–8794, 1988) describe a probe based on simultaneous hybridization of two DNA-based probes to close-lying sequences. One probe is modified in the 3'-terminus of the DNA chain with a donor fluorophore and the other probe is modified in the 5'-terminus with an acceptor fluorophore. When they are in proximity fluorescence energy is transferred from the donor to the acceptor fluorophore, which can be detected. The fluorophores are far apart in solution, but are brought together when the probes hybridize to TS by binding with the 3'-terminus of one probe next to the 5'-terminus of the other probe. The strategy has several disadvantages. It is necessary to distinguish fluorescence intensity of different wavelengths, since hybridization does not give rise to a significant change in total fluorescence, but only a change in the wavelength of fluorescence. The system is not suitable for quantitative determination of TS, since energy transfer efficiency depends on factors such as the distance between the fluorophores and their relative orientation (Förster, Ann. Phys. (Leipzig) 2:55–75, 1948), which may depend on the probed sequence. The strategy has fundamental problems with background fluorescence, since the light used to excite the donor does also to some degree excite the acceptor leading to a non-specific background signal. Finally, the requirement that two probes bind simultaneously to the target sequence results in slow hybridization kinetics making the technique less suitable for real time detection.

Another technique based on a pair of oligonucleotides was described by Morrison (EPA 87300195.2; U.S. Pat. No. 4,822,733; Analyt. Biochem. 183, 231–244, 1989; Biochem. 32, 3095–3104, 1993). These oligonucleotides are complementary to each other and also to the two strands of the target sequence. Both have a fluorophore in the 3'-terminus and a quencher in the 5'-terminus. When these pair with each other the quenchers at the 5'-terminus are in immediate proximity of the fluorophores at the 3'-terminus quenching their fluorescence. However, if the probe instead binds to TS fluorescence is observed. With this strategy one has two opposing design problems: It is desirable to have a high probe concentration to obtain fast hybridization kinetics, but simultaneously it is desirable to have a low probe concentration to minimize the background luminescence from free probes that have found neither TS nor a complementary probe to bind. Probing is performed by first heating the sample to separate the strands of both the probe molecules and the dsNA, and then the temperature is lowered to allow the probe to hybridize to TS. Unhybridized probe must, however, find a complementary probe to become quenched, until then it give rise to the same signal as probes hybridized to TS. Since probe is usually used in large excess, it make take considerable time before the background has dropped to an acceptable level making the strategy unsuitable for real-time detection. Finally, these probes are only applicable to double stranded TS. Tyagi, S., (PCT-WO 9513399; Nature biotech. 14, 303–307, 1989) describes 'molecular beacons' that are based on a probe with two chromophores, one at each end. These are chosen such that one chromophore quenches the fluorescence of the other when they are in proximity. The probe is designed to form secondary structure in solution that brings the two ends of the probe together, resulting in fluorescence quenching. This structural requirement is the first limitation of the probe since it must contain sequences that produces a particular secondary structure. As a consequence the probes are complementary also to other sequences than those they are designed to recognize, i.e., a probe is never unique for single TS. A further disadvantage is that probing is limited to a narrow temperature range, since both the hybrid between probe and TS and the secondary structure in the free probe must be stable. Temperatures at which TS does not hybridize to complementary NA, for example, can not be used. Further, thermal motion, which is significant already at room temperature, decreases the quenching efficiency, making it often necessary to use even lower probing temperatures, which decreases the specificity of the probing reaction.

One objective of the present invention is to overcome the limitations discussed above with traditional methods and also the limitations of the present homogeneous methods.

Further objectives with the present invention are:

that pretreatment of the sample, such as degradation to smaller fragments, should not be necessary, that target sequences are detected through hybridization with a probe that generates a signal, but which in non-hybridized state generates a much smaller, preferably negligible signal, that probing is possible in a homogeneous solution, that hybridization can be demonstrated rapidly, without delay, that the amount of NA can be quantified in real time, that particular NA sequences can be demonstrated in samples containing active enzymes, such as nucleases and proteases, that presence of a particular NA can be demonstrated in vivo, that the presence of a particular NA can be demonstrated with inexpensive equipment, that presence of an arbitrary sequence can be demonstrated selectively, that probing can be performed in a large temperature range, that people using the invention should not get exposed to hazardous chemicals, and that people using the probe should not require special training or particular experience.

To be able to utilize the entire potential of hybridization methods in diagnosis and research it is necessary to have a technique to detect hybridization in a solution using probes that by themselves generate low or negligible signals, but produce an observable response upon hybridization to target sequence. It is also desirable that the probe can be used in vivo without having a deleterious effect on tissue and cells. It should also allow real time detection. Of course, it should also be possible to use the probe for traditional hybridization. It is also desirable that the probe generates a signal that can be detected by the naked eye. The present invention fulfills these requirements to a reasonable degree.

BRIEF DESCRIPTION OF DRAWINGS

FIG. 15, illustrates the mass spectrum.

SUMMARY OF THE PRESENT INVENTION

Figure 1:
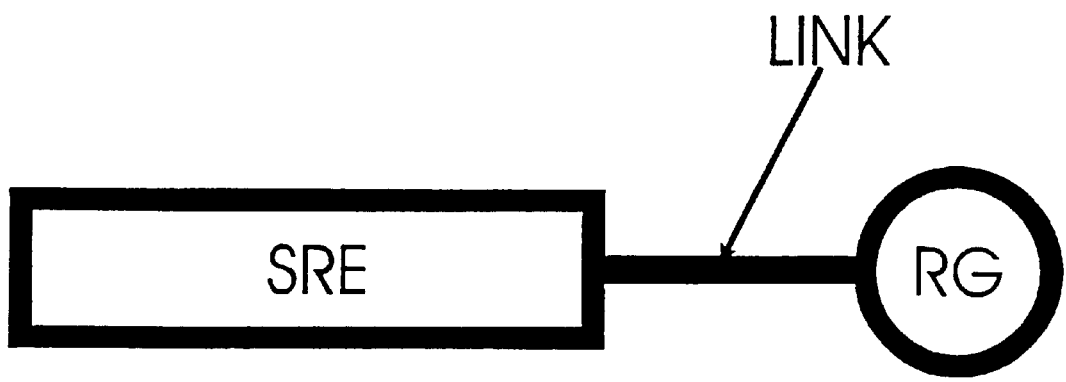
FIG. 1 is a drawing of the present invention. SRE, sequence recognizing element that binds specifically to a target sequence (TS); RG, reporter group that generates a signal upon hybridization; linker connecting SRE and RG.

The present invention is a probe composed of a sequence-recognizing element (SRE) and a reporter group (RG) joint by a linker (FIG. 1). RG is a compound characterized by having an observable property altered upon binding to nucleic acids (NAs). For example, it may have minimal luminescence free in solution and obtain strong luminescence when bound to NAs. SRE is a molecule that sequence specifically binds to NA, and is characterized by having a structure that minimizes its interaction with RG, or results in an interaction with RG that minimally affects its signal properties. It may be a NA whose bases at the terminal to which RG is attached are those for which RG has least affinity, or with which RG interacts in a way that minimally affects its signal properties. The SRE may also be structurally different from NA:s. It may be an oligodeoxyribonucleic acid analog (NAA) that has modified or replaced backbone, unnatural sugar moieties, different configuration and/or different stereochemistry. It may also be a peptide or protein that binds sequence specifically to nucleic acids. Of crucial importance is that the RG and SRE, when joint, interact with each other substantially differently than RG interacts with the target upon hybridization.

The here-invented probe exhibits a difference in a observable property (also referred to as signal property) upon binding to TS and can be used in a homogeneous assay, i.e., the presence of a particular NA can be detected without removing unhybridized probe. The here-invented probe can also be used in assays where the probe is immobilized, for example, by being tethered to a surface, having the advantage to present probes that the washing step required to remove unhybridized probe is less critical.

The here-invented probe may recognize TS in single-stranded (ss) NA as well as in double-stranded (ds) NA.

The here-invented probe may form complexes with ssNA that are more stable than dsNA, and may be used to probe dsNA at a temperature where its strands are separated.

The here-invented probe has a potential to be used for probing in vivo, both in cultivated cells and in whole organisms, where it has the advantage to traditional NA-based probes of being resistant to enzymes.

The here-invented probe gives rise to a signal that is proportional to the amount of TS and can be used to quantify the amount of a particular NA in a sample. This can be used to determine, for example, the amount of a particular PCR product in a complex mixture. It may also be possible to determine the amount of a particular RNA in, for example, cell extracts, or the relative concentration of two genes. The latter can, for example, be used to follow the progression of cancers.

The present invention generates a signal immediately upon hybridization and can be used to determine the amount of a particular NA in real time. This makes it possible to follow, for example, PCR reactions, in vitro transcription, etc., in real time. It should also be possible to monitor chances in the amount of a particular NA in cells in real time, for example, to follow the replication of chromosome or plasmid, or the production of a particular RNA.

The present invention can also be used to detect mutations. Probes can be constructed that hybridize more efficiently to a fully complementary sequence than to sequences that differ in one or a few bases.

The present invention has presupposition to be used to localize particular sequences in chromosomes by 'fluorescence in situ hybridization' (FISH) technique. Also here the present invention has advantages to traditional FISH-probes by its increase in fluorescence upon hybridization. To obtain sufficient signal intensity it may be necessary to hybridize several probes to the target sequence and/or equip them with many RG:s.

The present invention can be used, for example, to identify infectious agents (viruses, bacteria, parasites etc) in patients by detecting sequences specific for the foreign organisms, to test if individuals are predisposed, or suffer increased risk, to develop a disease by testing their genetic material, for prenatal diagnosis, to find genetic defects in embryos and fosters, and to predict complications in connection with, for example, birth delivery, to identify individuals in, for example, paternity tests, forensic tests, etc., to test the outcome in gene technological experiments, such as cloning, transfections, 'gene-knockouts' and the like.

DETAILED DESCRIPTION OF THE INVENTION AND ITS PREFERRED EMBODIMENTS

As indicated by the title, the present invention is a probe for detecting and quantifying nucleic acids (NAs) containing a particular target sequence (TS). In contrast to traditional methods, the present invention can be used for homogeneous probing; i.e., presence of TS can be demonstrated without removal of non-hybridized probe. Compared to existing homogeneous probing methods the present invention has at least one of the following advantages higher sensitivity, higher accuracy, and faster detection.

The present invention is a probe composed of a sequence recognizing element (SRE) and a reporter group (RG) that are linked (FIG. 1).

Figure 2:
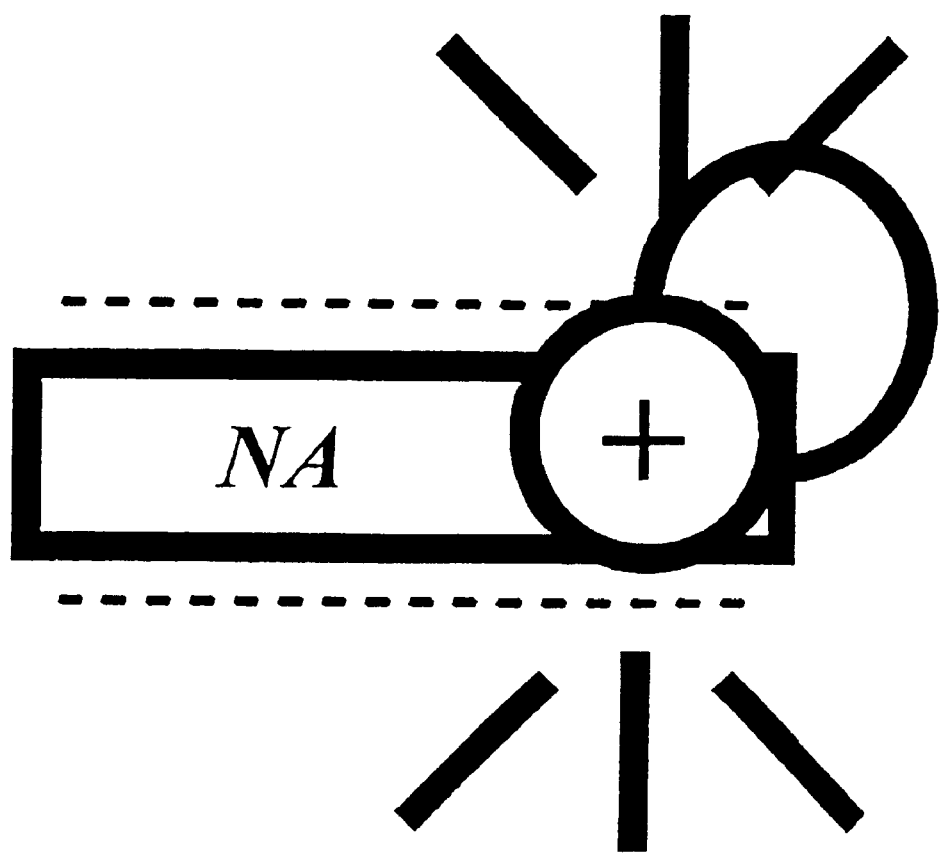
FIG. 2 illustrates back binding of RG. If SRE is too similar to natural nucleic acids, RG may fold back interacting with it such that a signal is generated. The probe is 'short-cut'.

Previous probes based on the SRE-RG concept have problem with a high background signal. When RG is a fluorofore, the free probe has considerable background luminescence and the increase in fluorescence intensity upon hybridization to TS is modest (less than fourfold, EP 0710 668 A2, Ishiguro et al., Nucl. Acids Res. 24, 4992, 1996). The large background signal is primarily due to that RG folds back onto the SRE and interacts with it (FIG. 2). The reason previous probes suffer this problem is that they have an SRE that is based on a NA, whose sequence structure has not been optimized to minimize the signal from RG. Since RG is a molecule that has affinity for NA:s (it must, otherwise it would not bind to TS upon hybridization), it will have a large tendency to fold back interacting with the SRE in any NA-based probe unless precautions are taken! This is a particularly important problem in probes where RG is a cation, as in fact used in all previous probes of this kind (EPO 710668; U.S. Pat. No. 5,157,032; Ishiguro et al., Nucl. Acids Res. 24, 4992, 1996), since the RG is attracted to the NA electrostatically.

The problems above are common to all NA-RG probes, no matter their signal property. It may be the interaction with electromagnetic radiation, as measured through changes in absorption or luminescence (fluorescence, phosphorescence), in steady-state or time resolved fashion, or a change in nmr response, redox potential, conductivity, reactivity etc. In all cases, probes based on NA:s with unoptimized sequences will suffer from back binding of the RG, and have undesired background signal.

The present invention describes SRE-RG probes, where the problem of RG folding back onto the SRE giving rise to background signal, is minimized. It also describes how the sequence of the probe, and the probing strategy, can be optimized to improve the change in the observable property of the probe. Finally, one form of SRE-RG probes is described that also exhibits a stronger signal upon binding to TS than corresponding NA-RG probes.

The Sequence Recognizing Element

Figure 3:
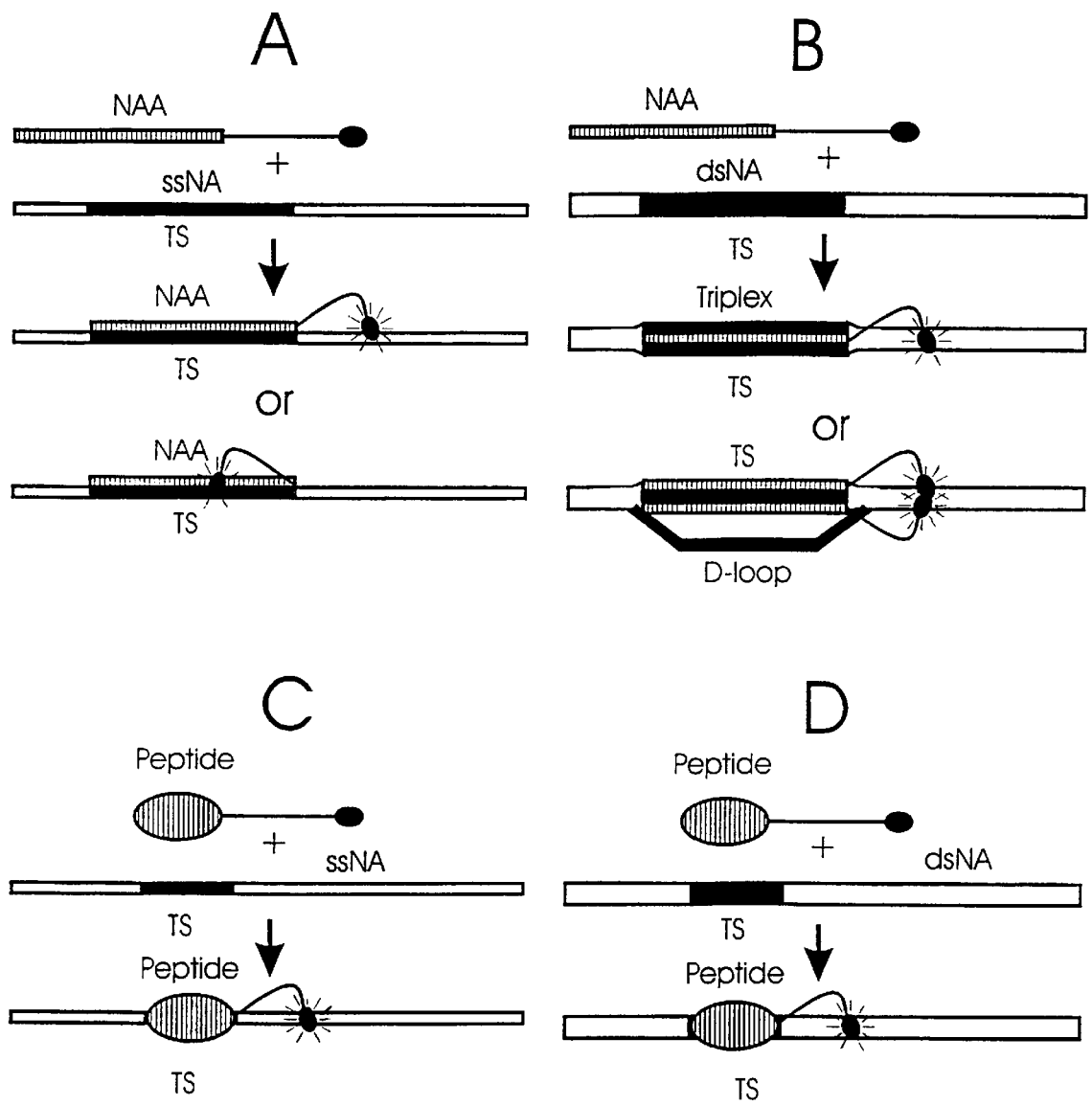
FIG. 3 illustrates probe designs and probing strategies. A) NAA-based probe recognizing ssTS. RG may bind to either the NAA/NA duplex or to the ssNA region next to TS. B) NAA-based probe recognizing dsTS by either forming a NAA:dsNA triplex with TS, or by forming a $NAA_2$:NA triplex via strand displacement. C) Peptide based probe recognizing ssTS. D) Peptide based probe recognizing dsTS.

The probe of the present invention is characterized by that the SRE element has a structure (either chemical or sequence or both) that either minimizes the interaction with RG, or interacts with RG such that it obtains minimal change in its signal properties. The SRE is either a NA, with a particular base or bases at the end to which RG is attached, or the SRE is chemically and/or structurally different from NA:s. It may be a nucleic acid analogue (NAA) (here equivalent to an oligonucleotide analogue) that is different from natural NA:s, but recognizes them through specific pairing between nucleotide bases. It may also be a peptide that binds sequence specifically to NA:s (FIG. 3), and it may be a combination of a peptide and a NAA, and, in an appropriate design, it may be a combination of a peptide and a NA. It may also be an organic synthetic molecule that binds to NA:s sequence specifically.

In the preferred embodiment the SRE is a NAA. With a NAA we refer to a linear polymer composed of units containing nucleotide bases, but differs from natural NA by having the phosphodiester backbone modified or replaced, or the sugar moieties modified or replaced, or has a different stereo chemistry, but interacts sequence specifically with NA through base-pair formation. The NAA must be sufficiently different from NA to it interact substantially differently with RG. Hence, NA derivatives (i.e., NA:s with one or several hydrogen atoms substituted by other groups), such as those that can be synthesized by commercial oligonucleotide synthesizers today, are not expected to be sufficiently dissimilar.

Minimum back binding is expected when the entire SRE is composed of NAA building blocks. However, a mixed NA/NAA polymer, designed such that RG is unable to fold back interacting with the NA steps, will also work. For example, NAA steps can be strategically placed to obstruct RG from folding back in a mixed polymer that contains mainly NA steps. In fact one properly chosen NAA step may be sufficient to stop RG from folding back if it is placed terminal in a NAA/NA copolymer. In the following, with NAA-based probes we also refer to probes with a SRE based on NAA-NA mixed polymers, that have at least one NAA step, and the RG is attached to a NAA step.

All the NAA steps in the SRE must not be identical. The SRE may also be a mixed polymer of NAA:s, NAA:s and NA, and also of NAA derivatives (NAA:s with one or several hydrogens replaced).

There are many NAA:s available that may be used, and novel ones are rapidly being developed owing to their potential of being useful in the unrelated area of antisense and antigene therapy (Nielsen, Annu. Rev. Biophys. Biomol. Struct. 24, 167, 1995; De Mesmaeker et al., Current Opinion in Structural Biology 5, 343, 1995). Examples of NAA:s are those that have modified phosphodiester linkages (phosphorothioates, methylphosphonates, boranophosphates, phosphoramidates, phosphoroselenoates, phosphotriesters, etc), those that have unnatural sugar moieties (homo-DNA, those with carbocyclic ringsystems, bicyclo-DNA etc), the phosphodiester analogues (alkanes, ethers, thioethers, amines, ketones, formacetals, thioformacetals, amides, carbamates, ureas, hydroxylamines, sulfamates, sulfamides, glycinyl amides, sulfones, etc.), those with complete replaced backbone (bicyclic riboacetal analogues, morpholino derivatives, peptide nucleic acids (PNA)), those with oligonucleotides linked 2',5', and those with α-nucleotide anomers.

Figure 4:
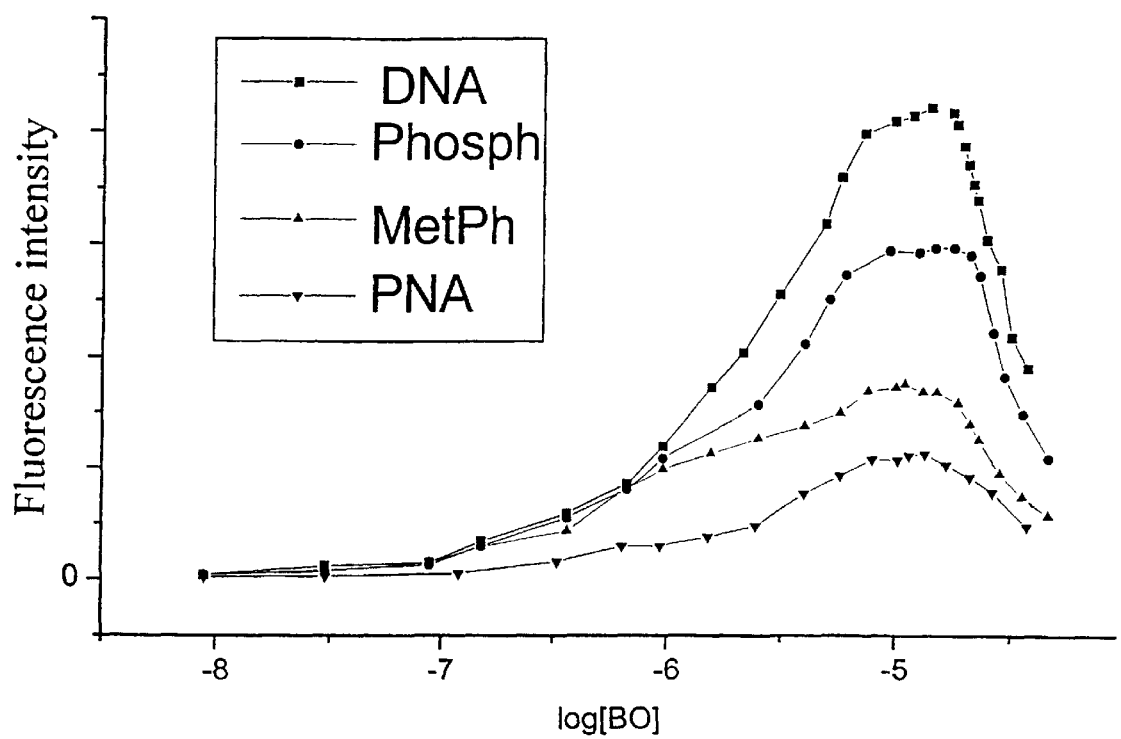
FIG. 4 illustrates comparison of the interaction of a compound, that has suitable properties for being used as RG in a probe, with NA and some NAA:s. Fluorescence of BO added to the single-stranded NAA:s, PNA, Methylphosphonates and Phosphorothioates, and ssNA (in the form of DNA). Considerably lower fluorescence is observed for the uncharged NAA:s, PNA and the Methylphosphonates. The NAA/NA had the same base compositions and their concentrations were 0.1 mM.
Figure 5:
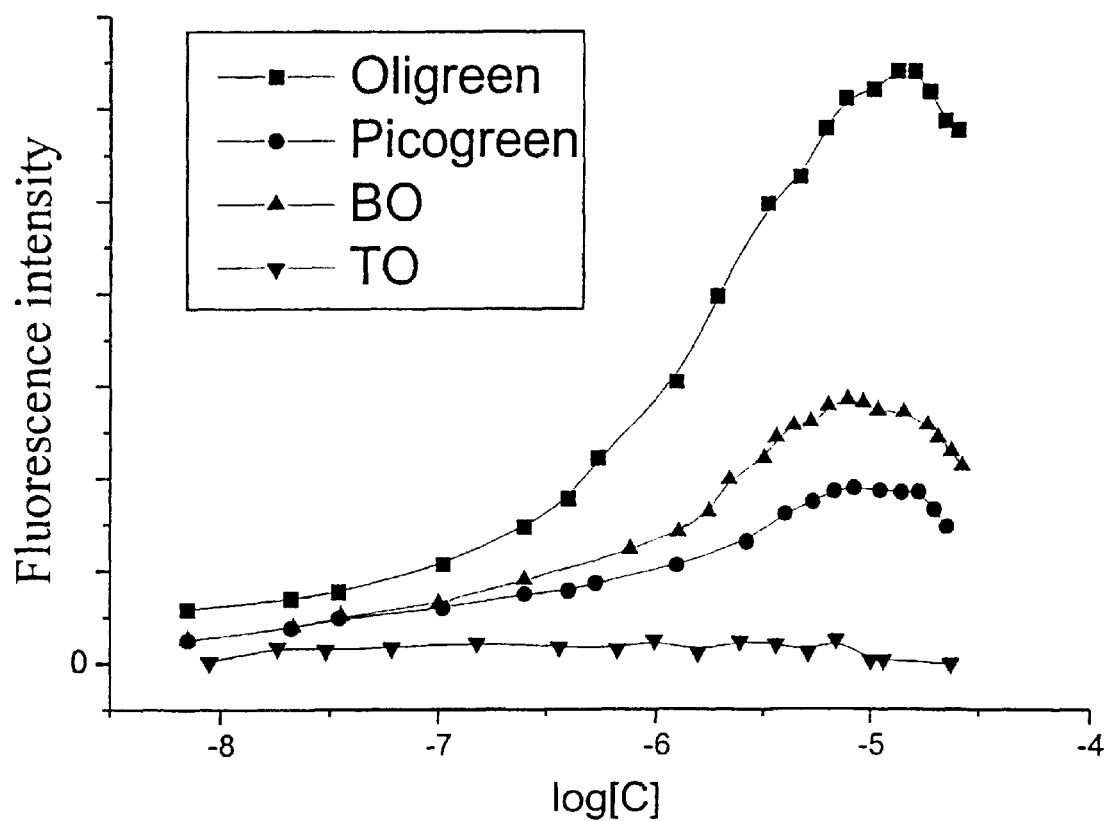
FIG. 5 illustrates comparison of the luminescence obtained by some asymmetric cyanine dyes in presence of PNA. The dye TO has essentially no luminescence at all. The dye Picogreen from Molecular Probes Inc. (structural formula not available) has low luminescence, as well as the dye BO. The dye oligreen, also from Molecular Probes Inc (structural formula not available), has the highest fluorescence. The PNA sequence was (H)-TTCTTCTTTT-(NH$_2$) (SEQ ID NO: 1) and the dye concentrations were about 0.1 mM (concentration of oligreen and picogreen are only approximate, since they are not provided by Molecular Probes Inc.).

Common to the NAA:s is that they are chemically, and therefore also structurally and electrostatically (at least in charge distribution), different from NAs, and hence may interact differently with compounds that are of interest to use as RG. This is exemplified in FIG. 4 with the compound BO. BO has essentially no luminescence by itself and becomes brightly luminescent when bound to NA. To be useful as RG in a SRE-RG probe, it shall not interact with the SRE in a way that gives rise to luminescence. As seen in FIG. 4 BO has considerably lower luminescence in presence of the uncharged NAA:s, PNA and methylphosphonates. In presence of the phosphorothioates it has about the same luminescence as with ssNA. This illustrates that replacing the NA for a NAA in a probe may reduce the signal from RG. But it also illustrates that any NAA may not do. Which NAA will work best will depend on what RG is. For example, if RG is a cation, such as BO, uncharged and cationic NAA:s are expected to work best. In general, since RG cannot have too low affinity for NA (it has to bind upon hybridization), there will always be an NAA for which RG has a lower affinity. If this NAA is used as SRE in a probe, the probe will generate a lower background signal than the corresponding NA-RG probe.

Small anionic molecules do not usually bind NA owing to electrostatic repulsion, while positive charged molecules have high affinity for NA. Hence most molecules of interest as RG are cationic, occasionally neutral, and rarely anionic. NAA:s that are uncharged, such as PNA:s, methylphosphonates, morpholino derivatives, and some of the phospliodiester analogues, are therefore of particular interest to use as SRE:s in the present invention, since they do not attract cationic RG electrostatically, and should exhibit less back binding than NA-based SRE. Of interest are also NAA:s that have some positive charges, such as neutral NAA:s into which positive charges have been introduced, for example, by modification of some residues, or by addition of positively charged substituents. Copolymers of uncharged and cationic NAA:s are also of interest. Of course, positive charges will reduce probe specificity, due to their non-specific electrostatic interaction with the NA. Therefore, the number of positive charges in the NAA should not be too high.

One of the best characterized NAA:s is the PNA-based on N-(2-amninoethyl)glycine units. This is the PNA we have in mind when we refer to a specific PNA. Its complex with nucleic acids is very different from dsNA (Eriksson & Nielsen, Nature Struct. Biol., 3, 410, 1996), and so is also the PNA duplex (H. Rasmussen, et al., Nature Struct. Biol. 4, 98–101, 1997). dsPNA forms both right and left handed helices, while PNA:DNA and dsDNA forms only right handed, dsPNA has 18 base-pairs per turn, PNA:DNA has 13 and dsDNA has 10, the base-twist in dsPNA is 19.8°, in PNA:DNA it is 28° and in dsDNA it is 34°. Hence, a compound that interacts in a particular way with ssNA is expected to interact quite differently with ssPNA, and, likewise, a compound that interacts in a particular way with dsNA is likely to interact differently with the PNA:NA hybrid. Therefore, a compound selected to have high affinity for NA, is expected to have a lower affinity for PNA, and for that matter also for most other NAA:s (FIG. 4). If such a compound is used as RG in a probe, it should exhibit less back binding, and hence a lower background signal, if the probe SRE is a NAA instead of a NA.

NAA:s have also other advantages to NA:s when used as SRE:s in probes. Since NAA:s are unnatural, they are resistant to enzymes, and NAA based probes can be used in cell extracts and other samples having enzymatic activity. NAA-based probes may also form more stable hybrids with TS than NA-based probes, allowing probing at higher temperature.

Figure 6:
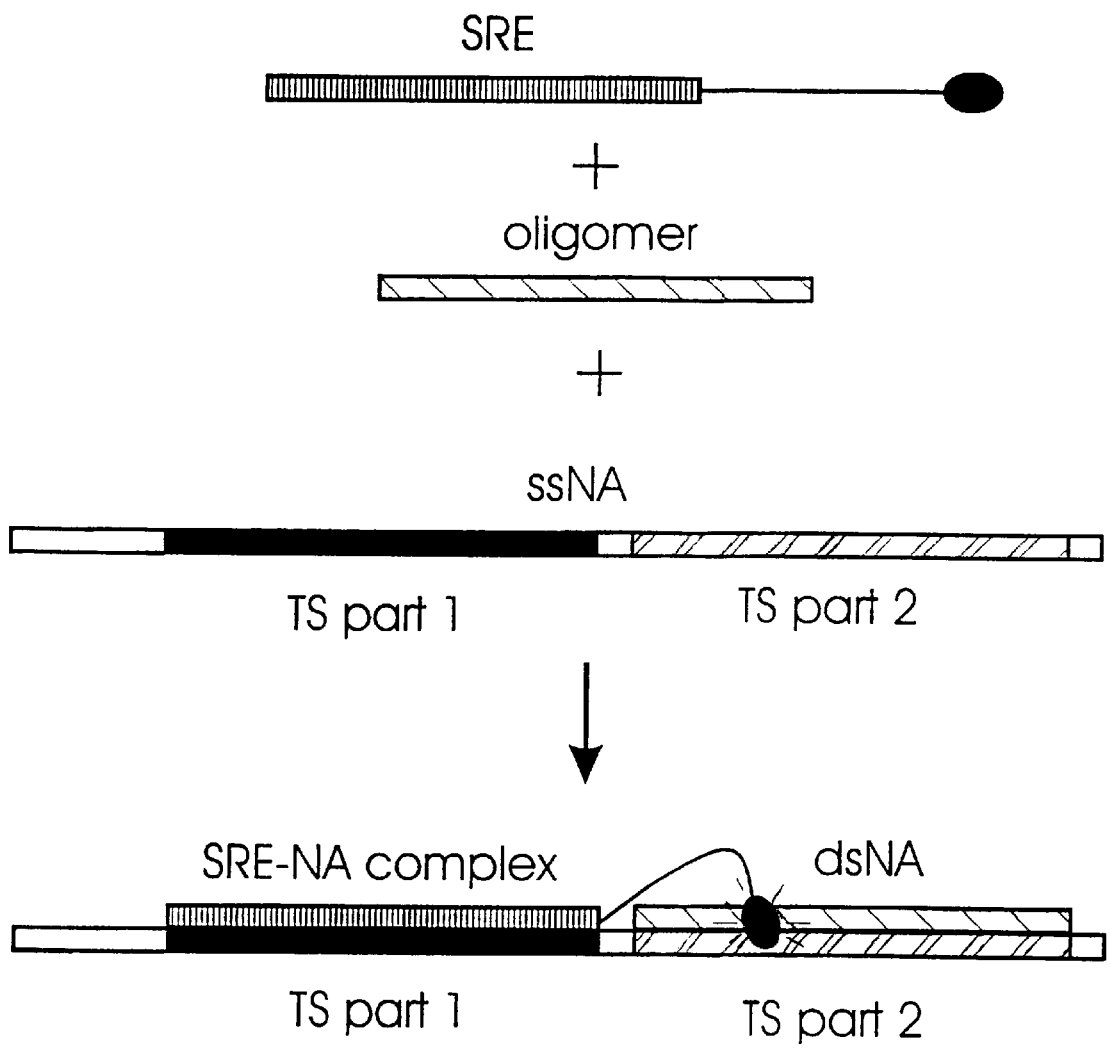
FIG. 6 illustrates alternative strategy to probe ssNA. A NAA-RG probe and an oligonucleotide are simultaneous hybridized to close-lying parts of a ssTS, and the oligonucleotide forms a duplex region to which RG can bind.
Figure 18:
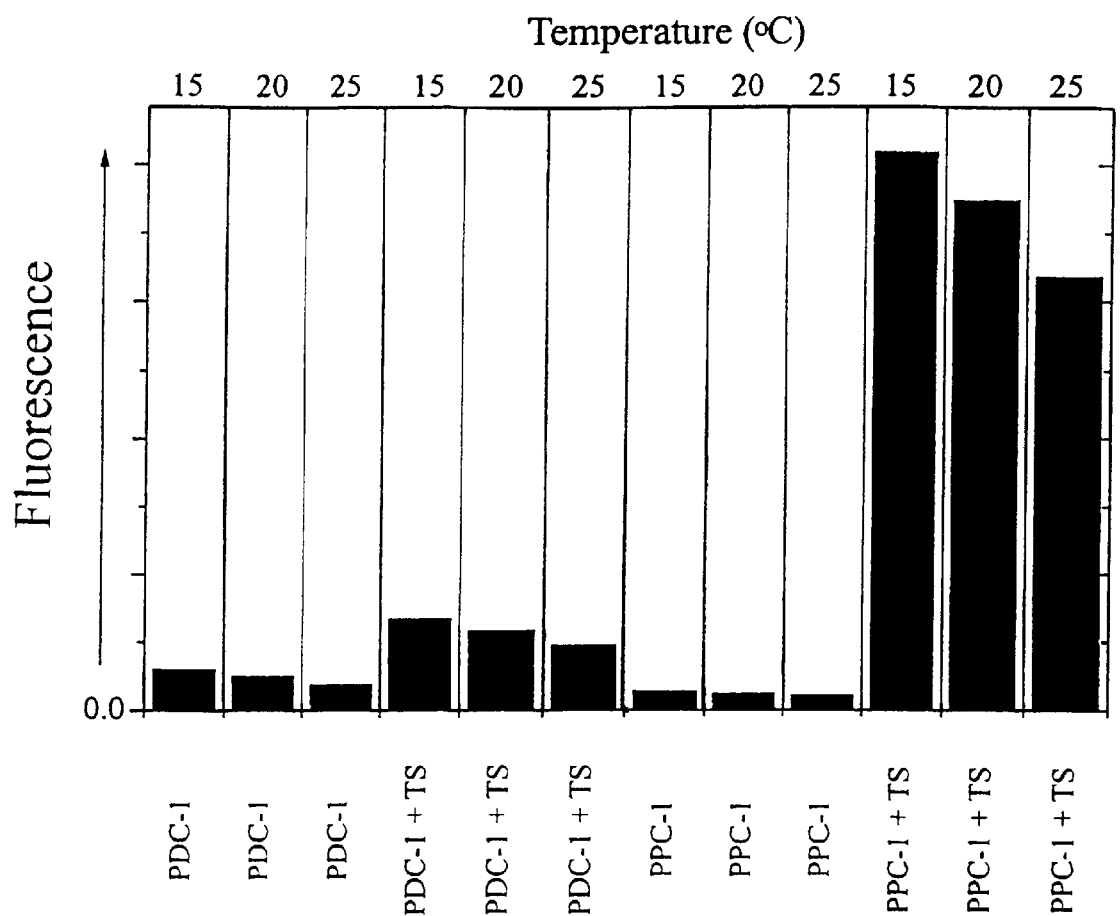
FIG. 18 illustrates the comparison of NAA and NA-based probes. Fluorescence of the free PNA-TO probe PP8-GCT-TO and the NA-TO probe PD8-GCT-TO, and of the same probes in presence of NA containing TS at the temperatures 15, 20 and 25° C. Experimental conditions were 20 mM borate buffer at pH 8.5 and 500 mM NaCl.

With NAA-based probes it is also possible to obtain a higher signal upon hybridization than with NA-based probes. Upon hybridization with ssTS the RG may bind either to the ssNA region next to TS or to the double-stranded region formed between the SRE and TS (FIG. 3A). If the SRE is a NAA, dsNA can be made available to RG by double-hybridization (FIG. 6). Hence, with an NAA-based probe the RG can always bind to the same kind of NA-structure as with a NA-based probe. However, when using NAA-based probes the RG can also bind to the NAA/NA hybrid, which may have a different structure in which RG obtains more intense signal. We have found this is the case with PNA (FIG. 18). The reason for this larger signal is unclear, but may be caused by that the uncharged PNA forms a more rigid duplex with NA than dsNA, which more effectively restricts the internal motion in the bound RG and increases its fluorescence signal. If this hypothesis is correct, similar effect is expected for many other NAA:s.

In another embodiment of the present invention the SRE is a protein or a peptide. These too are chemically very different from nucleic acids and may bind NA sequence-specifically. Today only a few sequence specific nucleic acid binding proteins are known, but methods are being developed to design peptides that specifically recognize a TS (Choo et al., Nature, 372, 642, 1994). RG:s can readily be attached to proteins and peptides (Example 10).

In another embodiment of the present invention the SRE is a NAA joined to a peptide, and the RG is linked to either the peptide or to the NAA. With this construction the advantages of both components may be obtained: the ability to recognize an arbitrary sequence by the NAA, and minimum interaction of the RG with the peptide. Combinations of peptides and PNA are particularly interesting, since they can be synthesized by the same solid phase chemistry and copolymers of essentially any kind can readily be made. For examples charges, to improve solubility and/or to repel charged RG:s, can be introduced using charged amino acids (Example 2).

In another embodiment of the present invention the SRE is a peptide-NA conjugate with the RG attached to the peptide. The peptide must be designed to obstruct interaction between the RG and the NA. A single bulky or suitably charged (i.e., like charge as RG) amino acid may be sufficient, though usually more amino acid residues will be required.

In still another embodiment SRE is a NA whose base or bases, at the end to which RG is attached, are those for which RG has least affinity and/or interacts in a way that minimally affects its signal properties.

The Reporter Group

RG is a molecule that delivers a readily detectable signal when, linked to SRE, binds TS. This signal should be significantly larger than any signal from RG linked to SRE in absence of TS. Since the number of structurally different NAA:s is very large, there is a good chance to find one that does not interact, or interacts in a way that does not give rise to the same change in the observable property of RG as natural NA:s do. Consequently, all compounds whose observable properties are altered upon binding to NA can be used as RG in combination with an appropriate SRE in a probe according to the present invention. The invention is illustrated by RG:s whose spectroscopic properties are altered upon binding to NAs, which is measured as a change in total fluorescence intensity. In the examples the fluorescence signal increases upon probe binding. This is, of course, not a limitation of the present invention. Probes with RG:s whose signal property decreases upon binding to TS can also be used.

Figure 12:
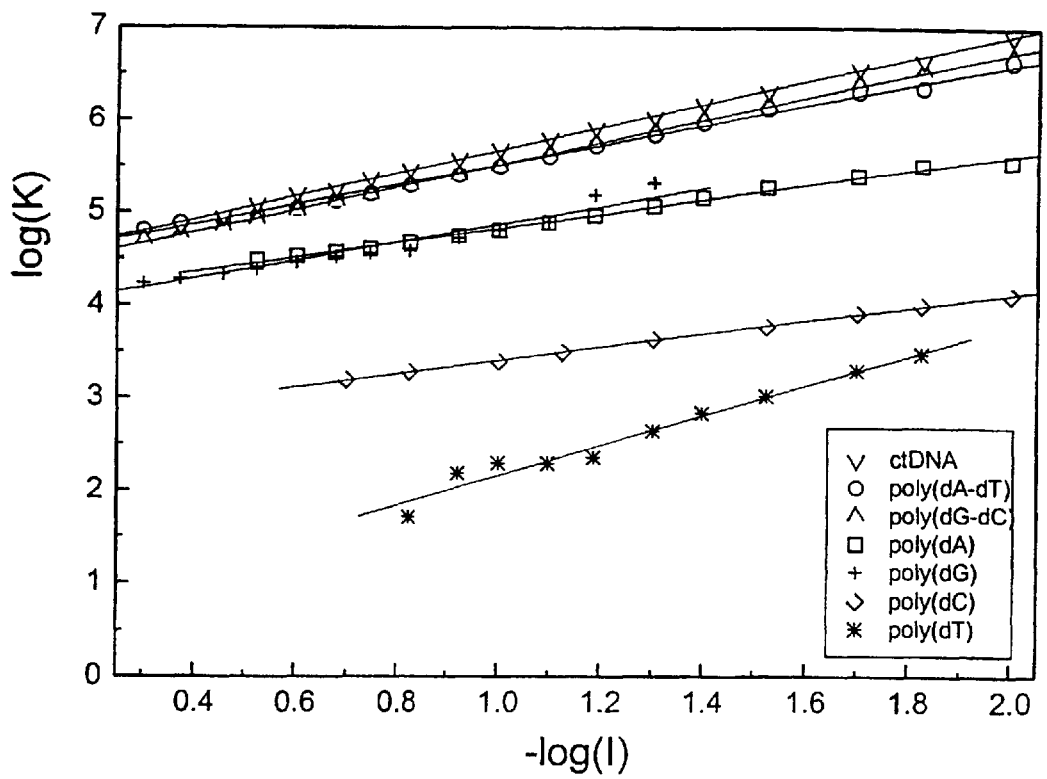
FIG. 12 illustrates the interaction of asymmetric cyanine dyes with various NAs. Top: the logarithm of the affinity constant of TO bound to various double and single-stranded NA:s as a function of ionic strength. The affinity for the polypyrimidines is considerably lower than for all other polymers. The data show that the affinity of the dye to the NA:s decrease logarithmically with the logarithm of the ionic strength. Bottom: Table summarizing binding properties of TO bound to the various NA:s. Two binding modes can be conceived. I, characterized by high affinity, high fluorescence and absorption at longer wavelength, is observed for all dsNAs and the polypurines and II, characterized by low affinity, low fluorescence and absorption at shorter wavelength observed for the polypyrimidines.

Compounds to be used as RG should have an affinity for NA that is sufficient to make them bind in hybridized state, but not too high, since it may lead to non-specific interaction of the probe with NA. The affinity of most ligands for NA:s depends on the ionic composition and temperature of the solution (Record et al., J. Mol. Biol. 107, 145, 1976), and can be moderated, often over several orders of magnitude (FIG. 12). To be suitable as RG in the present invention the compound should have an affinity for NA that is between 0.1 and $10^8$ M$^{-1}$ (-1<log K<8) in 100 mM ionic strength at room temperature.

Since luminescence can be detected with very high sensitivity, compounds that obtain an increase in fluorescence upon binding to NA:s are suitable as RG. Their quantum yield of luminescence should increase at least 10-fold upon binding NA, preferable at least 50-fold and more preferably at least 500-fold. Many such compounds are known. One of those with largest increase is thiazole orange (over 5000-fold, Rye et al., Nucl. Acids Res., 11, 2803, 1992).

The compounds should free in solution, i.e., in absence of NAs, have very low luminescence, since this gives rise to a background signal. The quantum yield of luminescence of the free compound should be less than 0.05, preferably less than 0.01 and more preferable less than 0.001.

The compounds should absorb light efficiently in the UV/VIS region. Its molar absorptivity at absorption maximum should be at least 1000 M$^{-1}$cm$^{-1}$, preferably at least 10,000 M$^{-1}$cm$^{-1}$, and more preferably at least 50,000 M$^{-1}$cm$^{-1}$.

The properties above are usually observed for compounds containing cyclic or polycyclic rings, out of which at least two, and usually no more than 5, are aromatic and may be joined. The rings may be carbocyclic or heterocyclic with usually 1–2 nitrogen atoms. Other common heteroatoms in these systems are oxygen and sulfur. The rings may be substituted with among other things alkyl groups, with usually 1–4 carbon atoms, oxygroups, such as hydroxy, alkoxy and carboxyesters, with usually 1–4 carbon atoms, amino groups, such as mono- and disubstituted amino groups, usually mono- and dialkylamino, with usually 0–6 carbon atoms, thiogroups, usually alkylthio with 1–4 carbon atoms, cyanogroups, non-oxo-carbonylgroups such as carboxygroups and their derivatives, usually carboxyamid and carboxyalkyl, with usually 1–7 carbon atoms, oxo-carbonyl and acyl, with usually 1–4 carbon atoms, halogen, with usually atomic number 9–35, etc.

Compounds of more interest are those containing two aromatic systems joined by a bond, containing for example ethylene groups, phosphate groups, amines, amides, carbonyls and carboxylesters, that is conjugated to the aromatic systems and therefore have some rigidity. These compounds have usually low luminescence free in solution owing to rotation around this bond, which leads to non-radiative deactivation from excited state. They obtain enhanced fluorescence when bound to nucleic acids, usually by intercalation or by binding in the minor groove, by being held in a planar conformation in the binding site unable to rotate around the conjugated bond. The rotation is also restricted in viscous solutions, which makes it possible to test if a compound has suitable properties (Carlsson et al., J. Phys. Chem., 98, 10313, 1994).

Of even more interest are asymmetric cyanine dyes (F. M. Hamer, in Heterocyclic compounds, Vol. 18 'Cyanine dyes and related compounds', 1964, Wiley & Sons), such as those described in (U.S. Pat. Nos. 4,883,867; 5,312,921; 5,321, 130; 5,401,847; 5,410,030; 5,436,134, 5,486,616), and particularly those with the structures shown below:

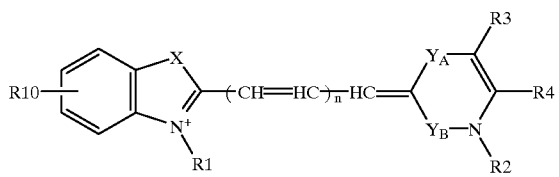

where $R^1$ is a hydrogen or to the nitrogen non-conjugated alkyl group of at most 6 carbon atoms, that may be substituted with polar residues such as hydroxyl groups, alkoxy groups, carboxyl groups and amino groups. X is O, S (or Se), N—$R^5$, where $R^5$ is hydrogen or a small alkyl group, or $CR^6R^7$, where $R^6$ and $R^7$ are hydrogens or alkyl groups. The first ring system is in these cases a benzoxazole, benzotiazole, benzimidazole and indoline, respectively. The other aromatic ring system may be a single or double aromatic ring, usually a quinoline or a pyridine. The side groups $R^2$, $R^3$ and $R^4$, which may be same, are hydrogen, small alkyl groups, aryles, or in pair, $R^2$ and $R^4$ or $R^3$ and $R^4$, and, in combination with two of the ring atoms, constitute a 5 or 6-membered aromatic ring, that may contain 0–2 heteroatoms such as O, S and N—$R^8$, where $R^8$ is an alkyl group. In the methine bond that connects the two aromatic systems n is 0, 1 or 2. This affects the distance and degree of conjugation between the ring systems and hence the wavelengths of absorption and emission (Griffith in 'Colour and constitution of organic molecules', Academic press, 1976). Y is HC=CH and its position is given by the indexes A and B, which are 0 or 1, if A=0 then B=1, and vice versa. With A=0 and B=1 we have:

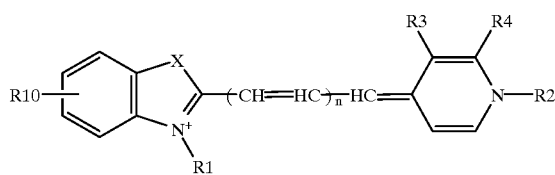

and with A=1 and B=0 we have:

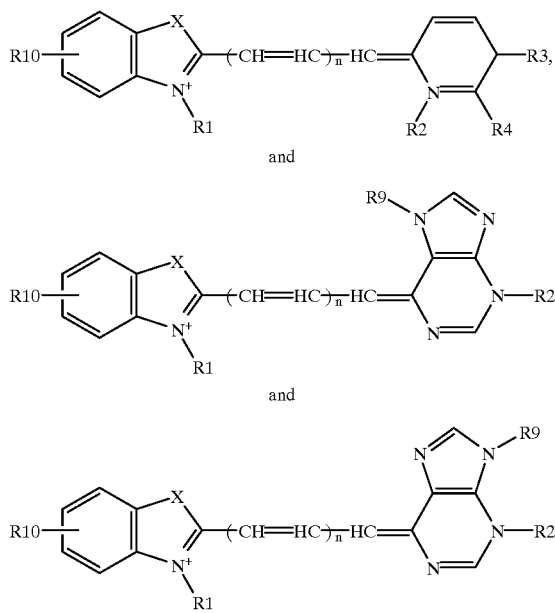

where $R^1$, $R^2$ and n are as above, and $R^9$ and $R^{10}$ are non-conjugated alkyl groups attached to the nitrogen, which may be substituted with polar residues such as hydroxyl groups, alkoxy groups, carboxyl groups and amino groups.

Homo- and heterodimers of the dyes can also be used in the present invention.

These compounds can be synthesized with established methods (Sprague, U.S. Pat. No. 2,269,234, 1942; Brooker et al., Houbenweyl methoden der organischen chemie, band V/1d, 1972; Lee et al., Cytometry 7, 508, 1986; Lee & Mize, EP 0410806, 1989). Their large enhancement in luminescence upon binding nucleic acids is well known (Lee & Chen, EP 0226272), and is exploited to detect reticulocytes (Lee & Chen, U.S. Pat. No. 4,883,867), parasites in blood (Lee & Mize, U.S. Pat. No. 4,937,198), to stain nucleic acids in electrophoresis (Quesada et al., Biotechniques 10, 616, 1991; Mathies and Huang, Nature 359, 167, 1992) and for ultra-sensitive detection of nucleic acids in capillary electrophoresis (Schwartz and Uhlfelder, Anal. Chem. 64, 1737, 1992). Substituted with polycationic chains (Glazer and Benson, U.S. Pat. No. 5,312,921; Yue et al., U.S. Pat. No. 5,321,130), and as homo and heterodimers (Yue and Haugland, U.S. Pat. No. 5,410,030), these compounds are among the most common dyes for staining nucleic acids.

Of particular interest for the present invention are asymmetric dyes, that we have invented (Example 5), which have a single carboxylic acid group that is not part of the conjugated system, and can be activated by coupling agents known in the field on solid phase peptide synthesis. Such dyes can be attached to, or incorporated into, peptides and peptide based NAA:s, such as the PNA:s, by methods known in the field of solid phase peptide synthesis, as described, for example, in Novabiochem 97/98 Catalogue & Peptide synthesis handbook.

The dyes used to illustrate the invention are referred to as TO and BO, and they have the chemical structures:

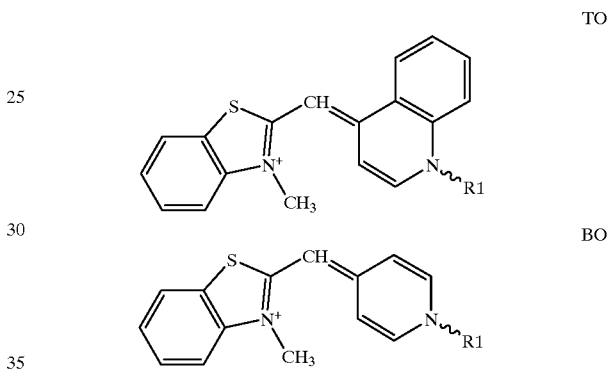

They have been synthesized with various side chains (Example 1) that allow attachment by either liquid (Example 3) or solid (Example 5) phase chemistry to various SRE:s.

We note that their oxygen analogues (i.e., same compounds but with oxygen in place of sulfur), and most likely also the selenium analogues, have very similar properties.

The affinities and luminescence properties of the asymmetric cyanine dyes depend on the base-sequence of the NA they interact with (FIG. 12). They bind with very high affinity to dsDNA, most likely by intercalation (Jacobsen et al., Nucl. Acids Res. 23, 753, 1995; Hansen et al., Nucl Acids Res., 24, 859, 1996). They bind somewhat weaker (<10 fold) to single-stranded polypurines, and considerably weaker (~100 fold) to single-stranded polypyrimidines. Also the fluorescence properties of the dyes depend on base sequence. The fluorescence is about 10 times more intense when they are bound to dsDNA and to polypurines than when they are bound to polypyrimidines. Differences are also seen in the absorption properties of the bound dye. Clearly the properties of the asymmetric cyanine dyes bound to NA:s depend very much on the base or bases with which they are interacting.

Molecules tethered to dsNA:s, and therefore most likely also to ssNA:s and NAA:s, interact mainly with the 1–3 outermost bases (Ciepek et al., J. Biomol. Struct. Dyn., 5, 361, 1987). Hence it is possible to minimize the background signal of NA-based and NAA-based probes by choosing the bases nearest the end to which RG is attached. These bases should be those for which RG has least affinity and/or with which RG interacts in a way that has minimal affect on its signal properties.

Figure 19:
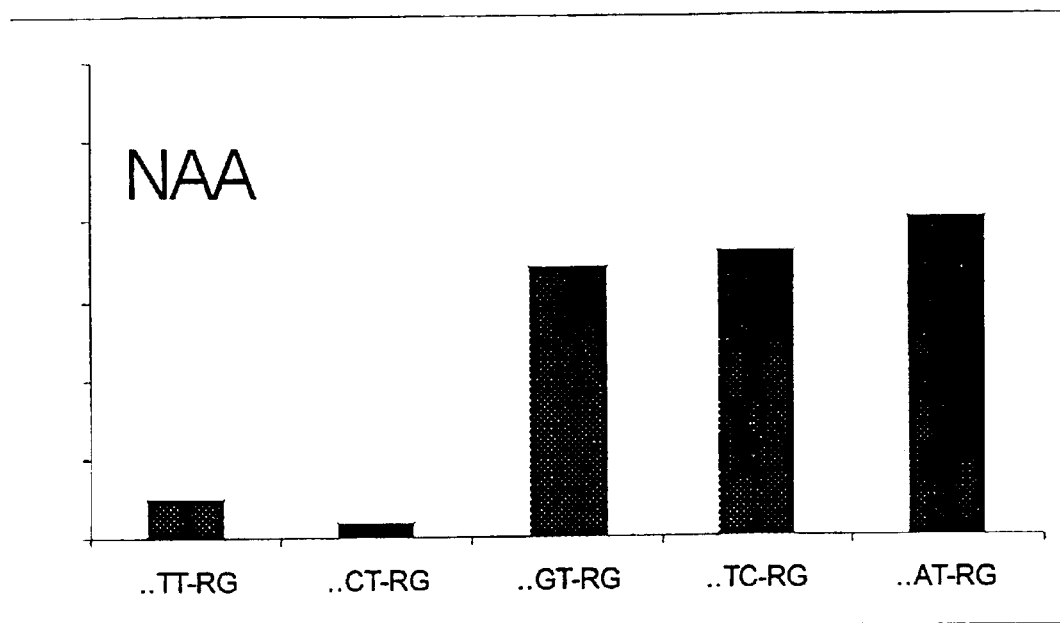
FIG. 19 illustrates the influence of endmost bases. Background fluorescence of NAA-RG (Top) and NA-RG (Bottom) probes having different bases at the end to which RG is attached. The NAA-RG data are averages of measurements obtained on PNA-based probes. The probes in each category had different sequences (but for the last two bases), charge, linker, RG (TO or BO), and the measurements were done at varying temperatures, pH and ionic strength. Still, within reasonable ranges, these parameters had little effect on the background signal compared to that of the endmost bases. NAA-based probes that ended . . . CT-RG and . . . TT-RG had the lowest background signal. The NA-based probes tested were identical, but for the last two bases (PD11-CXX-TO), and were characterized at same conditions (25° C., 10 mM Tris-buffer, pH 7.5, 1 mM EDTA, 10 mM NaCl). Also here the . . . CT-RG has lowest background. The data in the two graphs are not comparable, owing to different scaling and to the different condition used.
Figure 19:
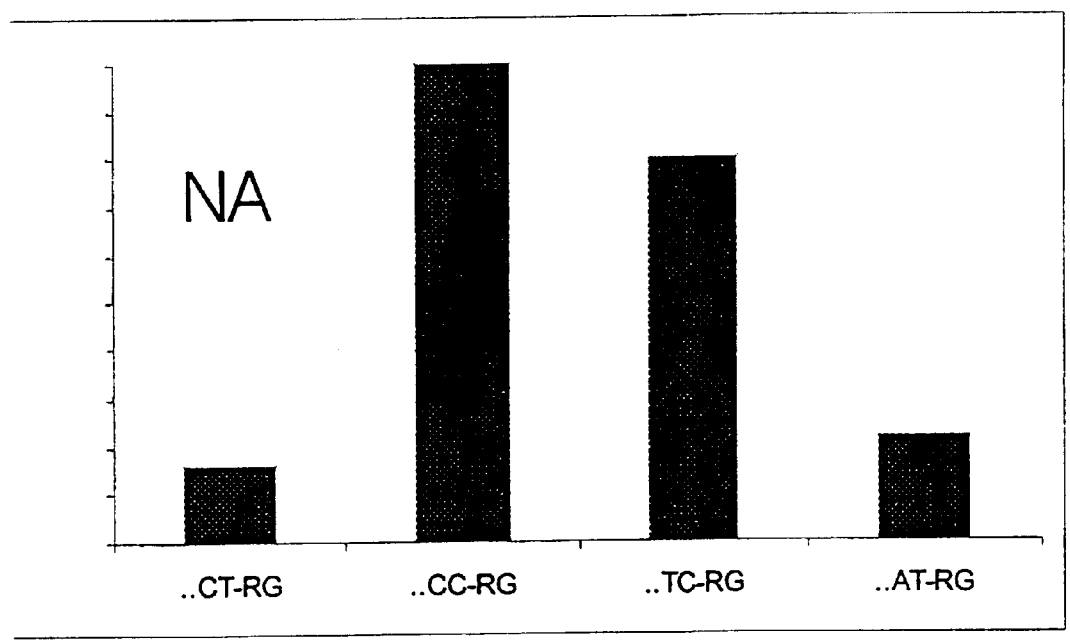

For the asymmetric cyanine dyes very low background luminescence is obtained when the endmost bases of the NA or NAA based SRE are . . . CT-RG or TT-RG (FIG. 19).

The situation is quite different with other RG:s. For example, the minor groove binder 4'-6,diamidino-2-phenyl indole (DAPI) has extensive luminescence when bound to a region of at least three consecutive A:T base-pairs, but considerably lower luminescence in any other sequences (Jansen et al., J. Amer. Chem. Soc., 115, 10527, 1993). Probes based on DAPI as SRE should therefore be designed not to have a run of three A:T base-pairs accessible to the tethered dye.

Conjugation of SRE and RG

To be joined SRE and RG must have suitable reactive groups. Many combinations are possible. Thiols, such as in cystein, can be joined to other thiols and to alkylating groups, such as iodoacetamide, various maleimides, derivatives of acrylic acid etc. Amino groups, such as the amino terminal and basic aminoacid residues in peptides, and in PNA, can be reacted with isothiocyanates, imidesters, such as succinimidesters and phthalimidesters, and sulfonhalides, glyoxals, aldehydes and ketones. Carboxylic acids, such as the carboxyl terminal in peptides and acidic amino acid residues, can be reacted with amines, hydrazin derivatives etc. These coupling reactions are well known in the art, and are described in, for example, the Novabiochem 97/98 Catalogue & Peptide synthesis handbook and the Handbook of Fluorescent Probes and Research Chemicals (sixth edition, Molecular Probes inc., ed. Richard Haugland).

When constructing derivatives of the dye it is important that the conjugated system is not affected, since it may ruin its spectroscopic properties. This usually means that the reactive group should be separated by at least one non-conjugated single bond from the aromatic system. For the cyanine compounds above, the reactive group can be put anywhere there is an R-group as long as it is separated by at least one $sp^3$-hybridized carbon from the aromatic system. It is, of course, also important that the RG derivative does not have side groups or other substituents that interfere with the coupling reaction.

The conjugation of SRE and RG is illustrated by two quite different approaches; one based on solution chemistry and one based on solid phase chemistry (Example 1).

Conjugation in aqueous solution of RG and SRE is exemplified using succinimidyl esters of asymmetric cyanine dyes and SRE:s with amino groups. In Example 4 the succinimidyl ester of TO (synthesized in Example 3) is attached to PNA, and in Example 10 the succinimidyl ester of BO is attached to a protein. The solution approach is very general, and can be used to attach essentially any RG to any SRE, by using suitable derivatives.

Solid phase conjugation of RG to SRE is exemplified by attaching novel carboxylic acid derivatives of the asymmetric cyanine dyes that we have developed (Example 5), to SRE:s with amino groups. In Example 6 a carboxylic acid derivatives of TO is attached to immobilized SRE of the kind PNA and in Example 7 a different carboxylic acid derivative of TO is attached to immobilized SRE-linker conjugate. The solid phase approach is particularly interesting for SRE:s of the kind peptides and PNA, since the dyes may be attached by the same procedure as the aminoacid residues and the PNA-bases, and complete probes can be synthesized using commercial peptide synthesizers.

The Linker

The main function of the linker is to keep the units together in a way that does not obstruct the interaction between RG and TS upon hybridization. The linker may be uncomplicated, such as a chemical single bond, but may also be complex containing, for example, functional groups. It may also be designed to obstruct the interaction between SRE and RG. Our results, based on modeling studies, show this may be accomplished by using short and/or stiff linkers, and linkers containing bulky groups. If RG is charged, like charges may be introduced into the linker to suppress back binding.

Many linkers can be constructed by joining SRE with suitable derivatives of RG (Example 1). More complex ones can be constructed by attaching additional units to either the SRE or the RG before joining them together (Example 7).

It is possible to moderate the affinity of the probe for NA by the design of the linker. Negative charges in the linker will decrease the affinity for NA, while positive charges will give rise to more stable hybrids. The latter are particularly interesting if probing is to be performed at higher temperature. Polar groups may also be introduced into the linker to increase probe solubility. It is also possible to construct linkers with several reactive groups to which RG:s can be attached. Such linker may be branched.

Figure 16:
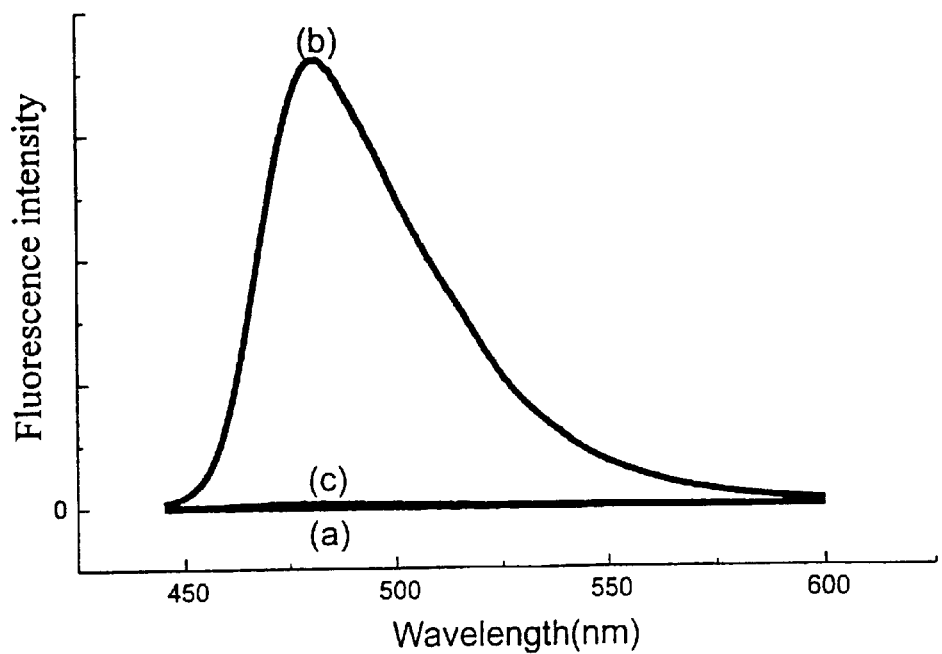
FIG. 16 illustrates the probing according to the design shown in FIG. 3D using probe EcoRI. A: fluorescence of free probe (a), probe in presence of dsNA containing EcoRI recognition sequence (b), probe in presence of non-complementary dsNA (c), Conditions used: (a) 0.5 $\mu$M probe; (b) 0.5 $\mu$M probe and 0.5 $\mu$M dsDNA molecules; (c) 0.5 $\mu$M probe and 0.5 $\mu$M poly(dAdT): poly(dAdT). B: Fluorescence of the same dye not bound to SRE in the presence of the same NAs. Fluorescence of free BO (a), BO in presence of dsNA (b), and BO in presence of poly(dAdT):poly(dAdT). Conditions: (a) 0.5 $\mu$M BO; (b) 0.5 $\mu$M BO and 0.5 $\mu$M dsDNA, (c) 0.5 $\mu$M probe and 0.5 $\mu$M poly(dAdT): poly(dAdT).
Figure 16:
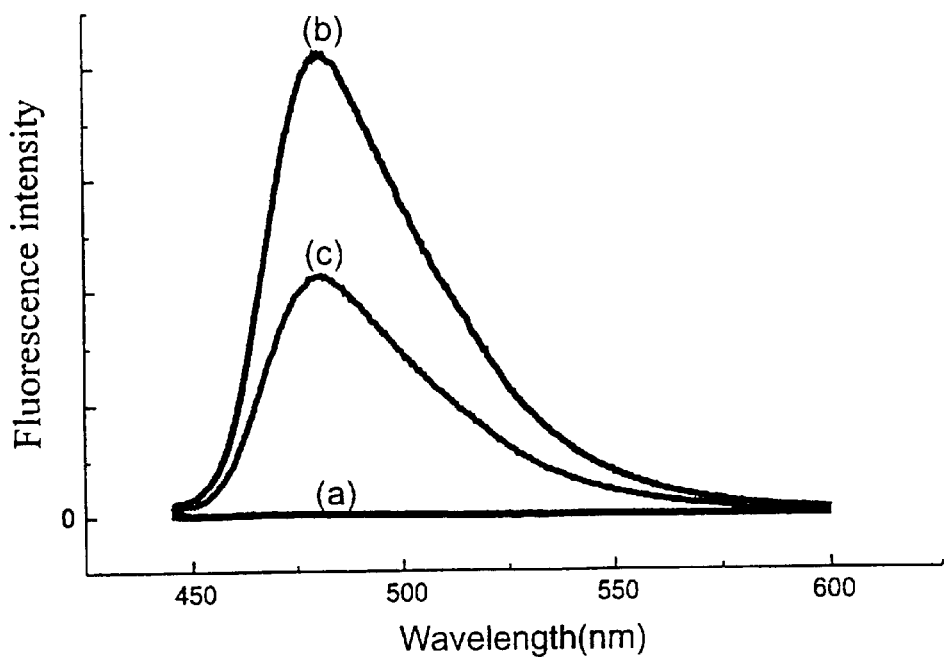

Peptide linkers are of particular interest in conjunction with RG:s based on asymmetric cyanine dyes since these have very low luminescence when attached to peptide chains (FIG. 16). Since PNA is synthesized by peptide chemistry, it can readily be extended by amino acids in either end. In fact, many of the PNA:s we have used have one or two lysines attached to the opposite end of the RG to increase probe solubility (Example 2). Aminoacids can also be introduced between PNA units. Peptide linkers of essentially any kind can be constructed. Stiff linkers can be made in the form of α-helices, charges can be introduced, and also functionality. Of course, other groups with carboxylic acid side chains may also be inserted into linkers by solid phase peptide synthesis (Example 7).

Peptide linkers could also be used to attach an RG to NA-based SRE:s. If properly designed the peptide linker may obstruct RG from interacting with the NA-bases.

Probing Strategies and Designs ssNA can be probed using a probe with an SRE that binds ssTS (FIGS. 3A and C). The SRE is usually a NAA (Example 2), but can also be a peptide, a peptide-NAA conjugate, a NA-NAA mixed polymer, or a designed NA-peptide conjugate. The size of TS may vary, depending on the system being probed. For example, quantifying the amount of a particular NA in a sample containing no, or only a few, other NA:s (i.e., such as the product of a PCR reaction), the probe may be as short as 5–6-bases, provided it forms stable hybrids and has sufficient sequence specificity. On the other hand, when probing the presence of a particular NA in a sample containing excess of other NAs, such as the presence of foreign NA against genomic DNA, the TS has to be longer. Probes recognizing 15–40 bases will work in most cases and length of 15–25 bases are likely to be sufficient for most human samples.

Figure 20:
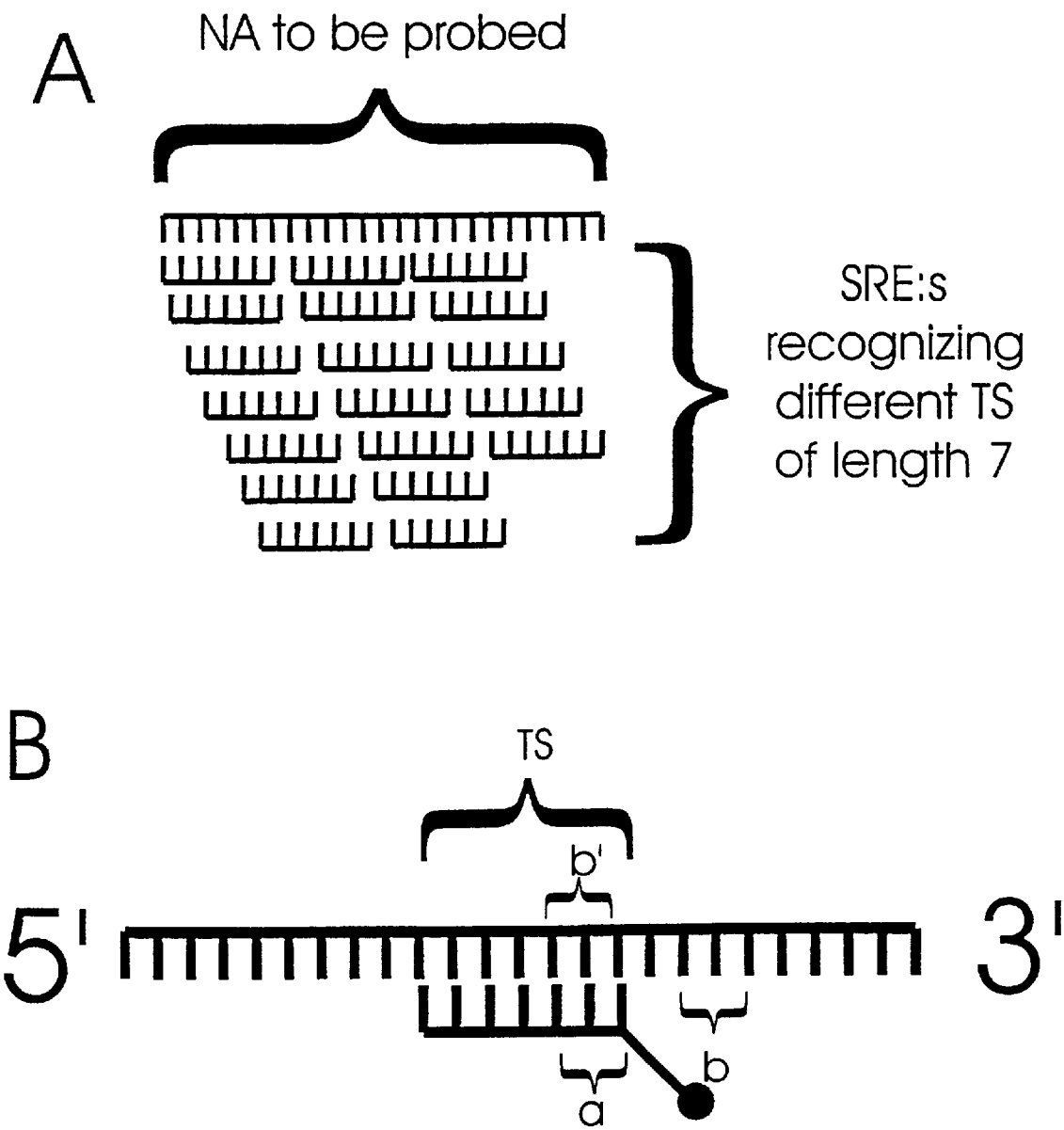
FIG. 20 illustrates the strategy to choose TS. The bases at the end closest to RG in hybridized state should be complementary to those for which RG has least affinity and/or with which RG obtains lowest signal (a), and it should be close to a site (b), or with the probe create a site (b'), that is in reach for RG in the hybridized state, for which RG has high affinity and with which RG obtains an intense signal upon binding.
Figure 21:
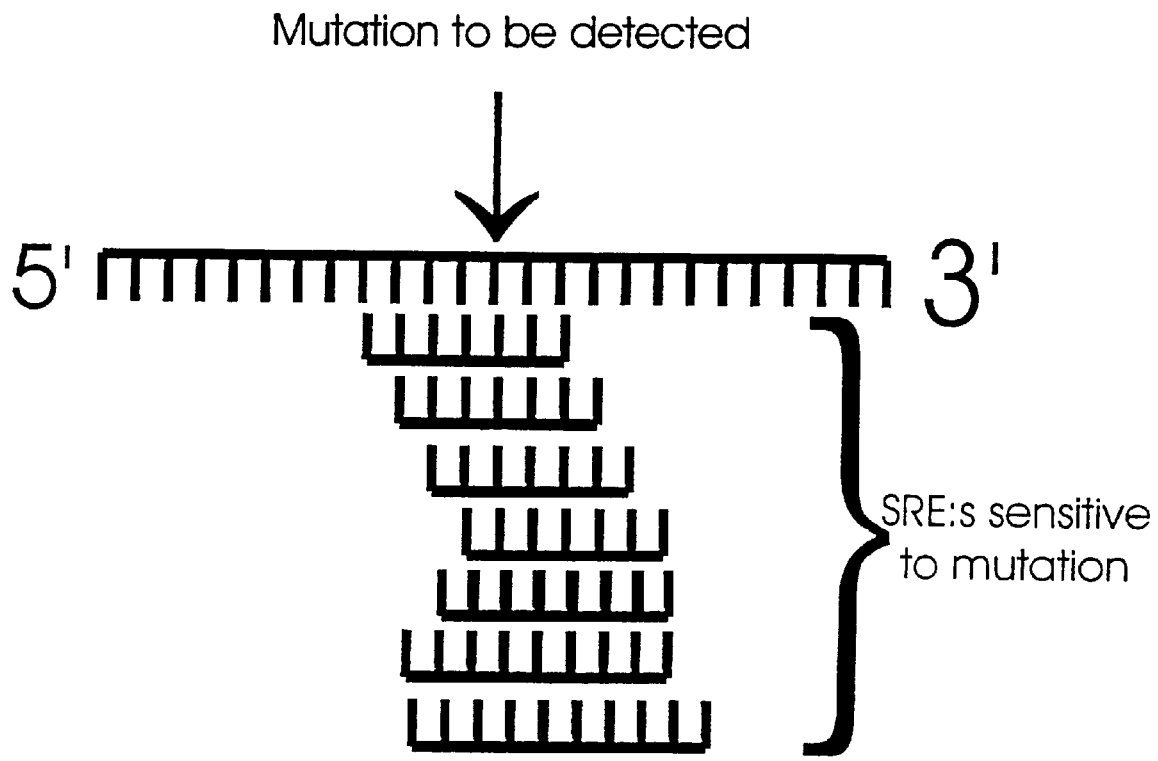
FIG. 21 illustrates the examples of probes sensitive to a particular mutation. TS of various lengths and with different varying overlap can be designed to sense a particular mutation. When choosing TS, one should consider the sequence structures with which RG may interact with a) in the free probe, and b) in the hybridized complex. This way it may be possible to design the probe such that low background luminescence is obtained, in combination with largest signal upon hybridization.

When probing the presence of a long NA fragment, such as a bacterial or viral genome, or the presence of a plasmid, a particular insert etc., the probe can be designed against many segments that all may be unique to this NA. For example, a 500 bases long NA fragment has 500−20+1=481 segments that are 20 bases long, which all may be unique to this NA. From the point of specificity, the probe can be designed to recognize any of these segments. When using NAA or NA-based probes one should chose a TS that at the end closest to RG in hybridized state has the base or bases complementary to those RG has least affinity for and/or in which presence RG obtains least signal. For RG:s based on asymmetric cyanine dyes, such as TO and BO, TS should end by . . . AA or . . . GA. It is also an advantage if TS is close to a site, or with the probe creates a site, that is in reach for RG in the hybridized state, for which RG has high affinity and when bound to it, obtains intense signal (FIG. 20). Similar strategy can by used to optimize the signal response of a probe that is sensitive to a particular mutation (FIG. 21).

dsNA can be probed at conditions, such as for example high temperature and low ionic strength, where its strands are separated, using a probe with an SRE that forms more stable hybrids with NA than a complementary NA. Such SRE:s are, for example, many uncharged and cationic NAA:s.

Native dsNA can be probed using a probe with a NAA that forms sequence specific triplexes or sequence specific D-loops as SRE, or a protein or peptide that binds dsNA as SRE (Example 10), or a protein/peptide-NAA/NA conjugate.

ssNA can also be probed by simultaneous hybridization of a probe according to this invention (based on NAA, peptide/protein, peptide-NAA conjugate or peptide-conjugate) and an oligonucleotide that are complementary to close lying regions of a TS, such that the oligonucleotide forms a duplex to which RG can bind (Example 9).

dsDNA can also be probed using two complementary probes that recognizes the two strands of TS. This approach counteracts renaturation and may produce larger signal response.

Probing can also be made with the probe immobilized to a solid support, preferable by a tether to SRE at the opposite end of RG. Such an approach could readily be automated, and the immobilized probes may even be reused.

Probing can also be made with the sample NA immobilized, as in many conventional approaches. Here the invented probe has the advantage that the washing step to remove non-hybridized probe is less critical.

Probes may be constructed with two RG:s, that may be different, and whose combined observable properties are altered upon hybridization. The probes can be designed as the NA-based probes with two pyrenes, as described by Yamana (Nucl. Acids Res. 11 (2–4), 383, 1992), or a fluorophore and quencher that quenches the fluorescence of the free probe by either intermolecular (Morrison, EPA 87300195.2) or intramolecular (Tyagi, WO 9513399) interactions. Here the invented probes have the advantage of forming more stable complexes (allowing probing at temperatures above the melting temperature of dsNA) and being resistant to nucleases. Of particular interest are probes where one RG is a fluorophore that obtains a large increase in fluorescence upon binding to NA:s, such as the asymmetric cyanine dyes, and the other is a quencher. In such a design the quencher would quench any residual fluorescence of the free probe, further improving the fluorescence enhancement upon hybridization.

Probing can also be performed in the presence of a third component that reduces the residual fluorescence of the free probe. The third component may be a quencher, i.e., a molecule that quenches the fluorescence of the RG in the free probe. The quencher could be free in solution, it could also be attached to the SRE, as described above, or it can be attached to another NA or NAA that is complementary to a part of SRE. This NA/NAA-quencher shall bind to the free probe in a way that brings the quencher into proximity of the RG. If the complementarity is only partial, the probe will have higher affinity for TS, and will dissociate from the NA/NAA-quencher if TS is present. The third component may also be an agent that binds RG and sequesters it from the back bound position in SRE. Different agents are likely to work best with different RG:s. Calixarene, for example, has large affinity for TO, and can be used to attenuate the background luminescence of SRE-TO probes (Example 12).

Probes of the present invention can be used to simultaneously detect and quantify the presence of several different NA:s in a sample, by constructing them with RG:s that have distinguishable spectral responses. They may, for example, emit light of different wavelengths.

The present invention may also be used localize sequences in chromosomes by Fluorescence in situ hybridization (FISH). Here the invented probes have the advantage to conventional probes that background signal from non-hybridized probes is considerably lower. Of particular interest are probes equipped with several RG:s, for example, attached to branched linkers, and to other SRE components, such as the backbone, sugar moieties and nucleotide bases of NAAs.

Detection of Hybridization

Binding of the probe to TS can be monitored by any observable property of the probe that is altered upon binding. Since fluorescence intensity can be measured with very high sensitivity by relatively inexpensive equipment, fluorescence detection is usually the method of choice. However, also changes in other observable properties can be monitored. Changes in fluorescence lifetime and fluorescence polarization can also be measured, as well as changes in absorption (FIG. 9), nmr response, conductivity etc.

Comparison of NAA-RG Based Probes with Prevalent NA-RG Based Probes

The advantages of the here-invented probes compared to prevalent probes is best realized by comparing one of the NAA-RG probes according to this invention with a NA-RG probe of the same sequence and with the same RG. Note that this way we only compare structural properties not related to sequence. For the comparison we use PNA as NAA and TO as RG. This means that the NA-RG probes are essentially identical to those described by Linn et al., (EP 0710 668 A2, U.S. Pat. No. 5,597,696), and very similar to those described by Ishiguro et al., (Nucl. Acids Res. 24, 4992, 1996), recalling that the dye oxazole yellow, YO, used by latter group, is in all essential aspects at most equivalent to thiazole orange.

From Example 14 follows that:

The PAA-based probes have lower background signal than the NA-based probes.

The PNA-based probes obtain higher signal than the NA-based probes when hybridized to TS.

The increase in signal response is considerably larger with the PNA-based probes than with the NA-based probes.

In addition, PNA-based probes have the following advantages to the NA-based probes:

PNA-based probes can be used at higher temperature than the NA-based probes, because they form more stable complexes with TS. The PP8-GCT-TO probe, for example, gives a 35-fold signal increase even at 45° C. (Example 11), at which temperature the corresponding NA-based probe would not form a duplex.

PNA-based probes can be used at any essentially any ionic strength, while probing with NA-based probes is very sensitive to ionic strength. In fact, the comparison in Example 14 was made at 500 mM NaCl to stabilize the NA-RG probe bound to TS.

PNA-probes are resistant to nucleases.

PNA:s, but not NA:s, can under some conditions invade dsDNA and form triplexes with one of the DNA strands via D-loop formation (Nielsen et al., Science 254, 1497, 1991).

EXAMPLES

Example 1
Synthesized RG:s

Example 3
Synthesis of a Succinimidyl Ester of Thiazole Orange (TO-5-S)

The synthesis was made in four steps.

N-methyl-2-methylbenzothiazole p-toluene sulphonate (I, FIG. 7) p-toluen methylsulphonate (3.5 g, 18.8 mole) was slowly added to 2.1 g (14.0 mole) 2-methyl benzothiazol in ethanol (10 ml). The mixture was refluxed for three hours and then stirred at room temperature for 15 hours. The solvent was evaporated and the product re-crystallized in methanol/acetone.

Yield: 4.2 g, 12.6 mmol, 91%.

Figure 7:
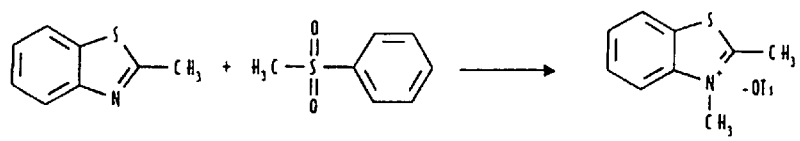
FIG. 7 illustrates synthesis of TO-5-S.
Figure 7:
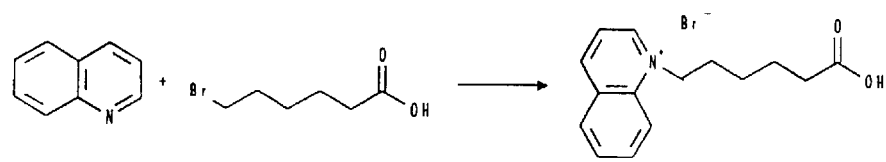
Figure 7:
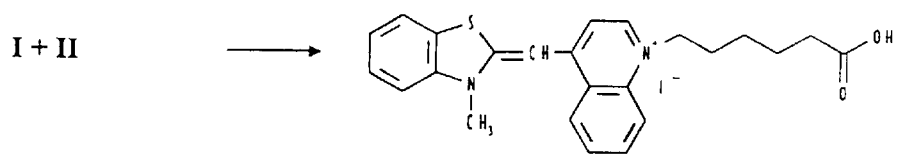
Figure 7:
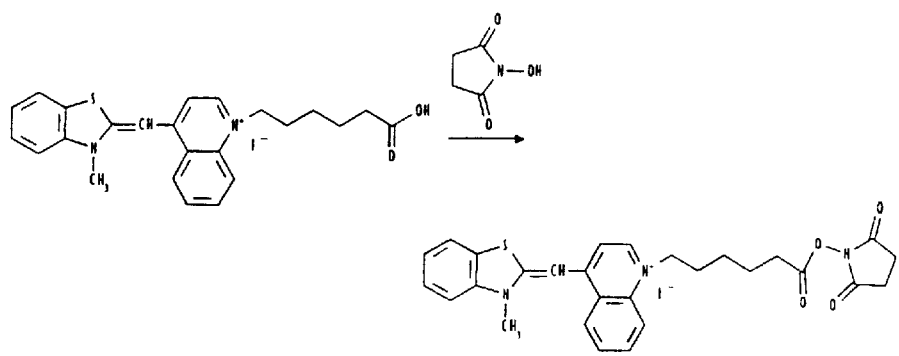

N-(carboxypentyl) quinoline bromide (II, FIG. 7)

Chinolin (5.2 g, 40 mmol) and 6-bromo-hexanicacid (7.8 g, 40 mmol) was added to 30 ml acetonitrile. The mixture was refluxed under nitrogen atmosphere for three hours and

| Dye | $R_1$ | For attachment by | Used in probes |
|---|---|---|---|
| TO-1-O | $-(CH_2)_1-COOH$ | Solid phase | — |
| TO-2-O | $-(CH_2)_2-COOH$ | Solid phase | PP16-GTC-TOb, PP16-GTC-TOc |
| TO-5-O | $-(CH_2)_5-COOH$ | Solid phase | PP11-TT-TO, PP8-GCT-TO, PP5-GCT-TO, PP15-TGT-TO, PP16-GTC-TOa |
| TO-10-O | $-(CH_2)_{10}-COOH$ | Solid phase | — |
| TO-1-S | $-(CH_2)_1-CO-O-C_4O_2NH_4$ | Solution | — |
| TO-2-S | $-(CH_2)_2-CO-O-C_4O_2NH_4$ | Solution | — |
| TO-5-S | $-(CH_2)_5-CO-O-C_4O_2NH_4$ | Solution | PP10-CTT-TO, PD8-GCT-TO, PD10-CTT-TO |
| BO-1-O | $-(CH_2)_1-COOH$ | Solid phase | — |
| BO-2-O | $-(CH_2)_2-COOH$ | Solid phase | — |
| BO-10-O | $-(CH_2)_{10}-COOH$ | Solid phase | PP15-TGT-BO |
| BO-1-S | $-(CH_2)_1-CO-O-C_4O_2NH_4$ | Solution | — |
| BO-2-S | $-(CH_2)_2-CO-O-C_4O_2NH_4$ | Solution | — |
| BO-10-S | $-(CH_2)_{10}-CO-O-C_4O_2NH_4$ | Solution | PP10-CTT-BO, PP15-GAT-BO, EcoRI |

$R_1$ is the side chain containing the reactive group by which RG is attached to the SRE.

Example 2
Probes Synthesized then stirred for 15 hours at room temperature. 50 ml acetone was added and the solution was stirred for further 1 hour.

| Code | SRE | RG | Linker | Sequence | | |
|---|---|---|---|---|---|---|
| NAA based probes[1] | | | | | | |
| PP10-CTT-TO | PNA | TO | $-(CH_2)_5-CO-NH-(CH_2)_5-CO-$ | (H)-TTCTTCTTTT-$(NH_2)$ | | (SEQ ID NO:1) |
| PP10-CTT-BO | PNA | BO | $-(CH_2)_{10}-CO-NH-(CH_2)_5-CO-$ | (H)-TTCTTCTTTT-$(NH_2)$ | | (SEQ ID NO:1) |
| PP11-TT-TO | PNA | TO | $-(CH_2)_5-CO-$ | (H)-TTCTCGTCGAT-Lys$^+$-$(NH_2)$ | | (SEQ ID NO:2) |
| PPS-GCT-TO | PNA | TO | $-(CH_2)_5-CO-$ | (H)-TCGTCGAT-Lys$^+$-$(NH_2)$ | | (SEQ ID NO:3) |
| PP5-GCT-TO | PNA | TO | $-(CH_2)_5-CO-$ | (H)-TCGAT-Lys$^+$-$(NH_2)$ | | (SEQ ID NO:4) |
| PP15-TGT-TO | PNA | TO | $-(CH_2)_5-CO-$ | (H)-TGTACGTCACAACTA-Lys$^+$-Lys$^+$-$(NH_2)$ | | (SEQ ID NO:5) |
| PP15-TGT-BO | PNA | BO | $-(CH_2)_{10}-CO-$ | (H)-TGTACGTCACAACTA-Lys$^+$-Lys$^+$-$(NH_2)$ | | (SEQ ID NO:5) |
| PP16-GTC-TOa | PNA | TO | $-(CH_2)_5-CO-$ | (H)-CTGTACGTCACAACTA-Lys$^+$-Lys$^+$-$(NH_2)$ | | (SEQ ID NO:6) |
| PP16-GTC-TOb | PNA | TO | $-(CH_2)_2-CO-$ | (H)-CTGTACGTCACAACTA-Lys$^+$-Lys$^+$-$(NH_2)$ | | (SEQ ID NO:6) |
| PP16-GTC-TOc | PNA | TO | $-(CH_2)_2-C_4N_2H_8-CH_2-CO-$[2] | (H)-CTGTACGTCACAACTA-Lys$^+$-Lys$^+$-$(NH_2)$ | | (SEQ ID NO:6) |
| P15-GAT-BO | PNA | BO | $-(CH_2)_{10}-CO-$ | (H)-TAGTTGTGACGTACA-$(NH_2)$ | | (SEQ ID NO:7) |
| Peptide based probes | | | | | | |
| EcoRI | Peptide | BO | $-(CH_2)_{10}-CO-$ | EcoRI aminoacid sequence | | |
| NA-based probes[3] | | | | | | |
| PD8-GCT-TO | DNA | TO | $-(CH_2)_5-CO-NH-(CH_2)_5-CO-$ | (5') TCGTCGAT (3') | | (SEQ ID NO:3) |
| PD10-CTT-TO | DNA | TO | $-(CH_2)_5-CO-NH-(CH_2)_5-CO-$ | (5') TTCTTCTTTT (3') | | (SEQ ID NO:1) |
| PD11-CTT-TO | DNA | TO | $-(CH_2)_5-CO-NH-(CH_2)_5-CO-$ | (5') TTCTCGTCGAT (3') | | (SEQ ID NO:2) |
| PD11-CAT-TO | DNA | TO | $-(CH_2)_5-CO-NH-(CH_2)_5-CO-$ | (5') TACTCGTCGAT (3') | | (SEQ ID NO:8) |
| PD11-CTC-TO | DNA | TO | $-(CH_2)_5-CO-NH-(CH_2)_5-CO-$ | (5') CTCTCGTCGAT (3') | | (SEQ ID NO:9) |
| PD11-CCT-TO | DNA | TO | $-(CH_2)_5-CO-NH-(CH_2)_5-CO-$ | (5') CTCTCGTCGAT (3') | | (SEQ ID NO:9) |

[1](H) symbolizes a free aminogroup and $(NH_2)$ symbolizes a terminal carboxamide.
[2]Stiff linker.
[3]Oligodeoxyribonucleotides with amine linker were purchased from Scandinavian Gene Synthesis. Succinimidyl ester of TO was attached and the probe was purified by the same procedure as the PNA-based probe in Example 4, except that TFA was replaced by 0.1 M TEAA (triethylammonium acetate), pH 7.0.

The white precipitate was filtered, washed with acetone (2*10 ml) and dried.

Yield: 8.4 g, 26 mmol, 65%.

N-carboxypentyl-4-[(3-methyl-2(3H)-benzothiazolyliden)methyl]-quinoline iodide (III, FIG. 7)

III was synthesized by condensation (reflux for 45 min) of I (1.6 g, 5 mmol) and II (4.8 g, 15 mmol) in presence of KOH (0.8 g, 15 mmol) in ethanol (20 ml). After cooling to room temperature the product was precipitated with 30% KI (aq.) (20 ml). The precipitate was filtered, washed with acetone and re-crystallized in methanol.

Yield: 1.0 g, 2 mmol, 40%.

N-hydroxysuccinimidyl ester of III (TO-5-S) (FIG. 7)

III (0.5 g, 1 mmol) and hydroxysuccinimid (0.11 g, 1 mmol) was dissolved in 25 ml (dry) dimetoxyethane. Dicyclohexylcarbodiimid (0.23 g, 1.1 mmol) was added to the cold solution. The solution was stirred at 0° C. for 20 hours, and urea was removed by filtration. The filtrate was concentrated and the sample re-crystallized in methanol.

Yield 0.4 g, 0.65 mmol, 65%.

Example 4

Figure 9:
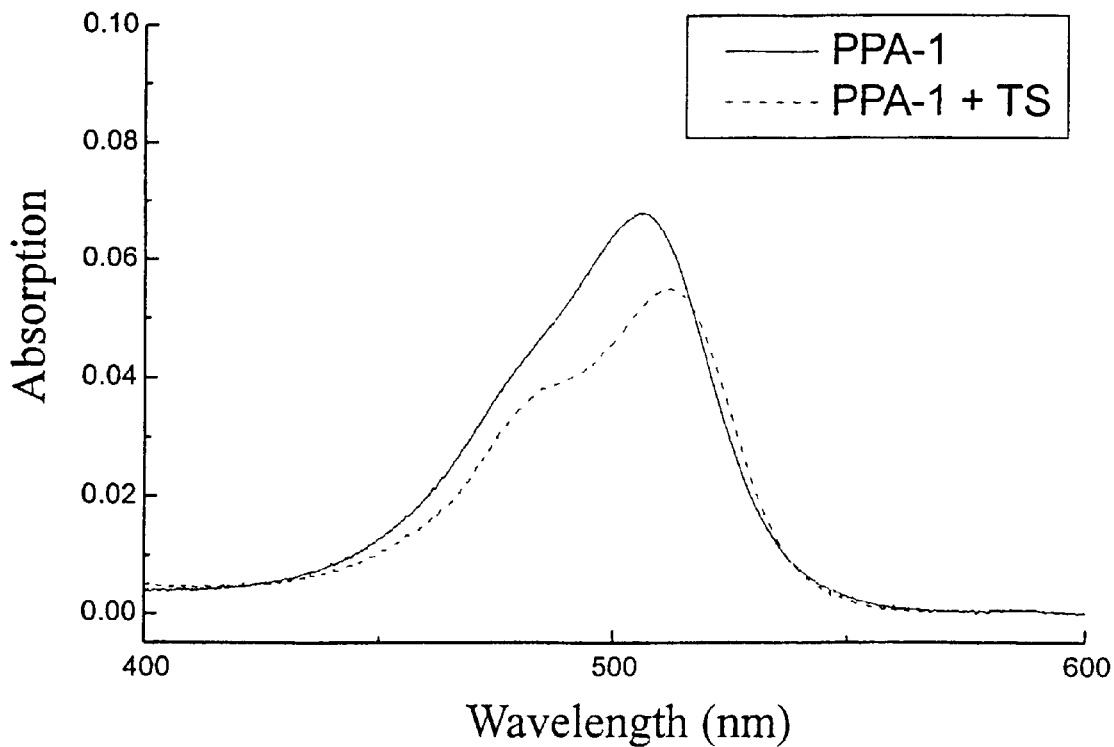
FIG. 9 illustrates the absorption spectra of free and hybridized probe. Absorption spectra of the dye region (400–600 nm) of free and to TS hybridized probe PP10-CTT-TO. Upon hybridization the dye spectrum shifts to longer wavelength and the overall intensity drops. These changes can be exploited to monitor hybridization in homogeneous solution.

Solution Synthesis of a PNA Probe (PP10-CTT-TO) and Characterization Thereof 38 nmol of a PNA, equipped with an amino group, of the sequence 'TTTTCTTCTT-CO—$(CH_2)_5$-(SEQ ID NO:10) $NH_2$' was dissolved in 10 μl $H_2O$, and 31 μl of 500 mM $Na_3BO_3$ buffer, and 10 μl of dioxane was added. The reaction was started by addition of 140 nmol TO-5-S (in DMSO) in two aliquots of 2 μl (with 5 minutes stirring in between), where after the reaction mixture was placed at 37° C. for four hours. After cooling to 25° C. 10 μl of acetonitrile was added. The product was purified by HPLC, using a reversed phase C-18 column (Waters, symmetry C18 3.9× 150 mm) in a gradient system (LKB 2249), and monitoring absorption at 260 nm (LKB 2151). The gradient used was a mixture of acetonitrile and water with 0.01–0.1% v/v trifluoroacetic acid. The flow was 1 ml/min and the gradient was 95–60% $H_2O$, 20 min., 60–0% $H_2O$, 5 min. Probe and excess TO-5-S were well separated. Fractions containing the probe were frozen with liquid nitrogen and freeze-dried for 15 hours to removed solvent and the trifluoroacetic acid. This gave a loose reddish material that was dissolved in deionized water. The probe was hybridized to TS, which resulted in a large change in RG absorption revealing its interaction (FIG. 9).

Example 5

Synthesis of a BO-2-O ($R_1$=$CH_2CH_2COOH$)

Figure 14:
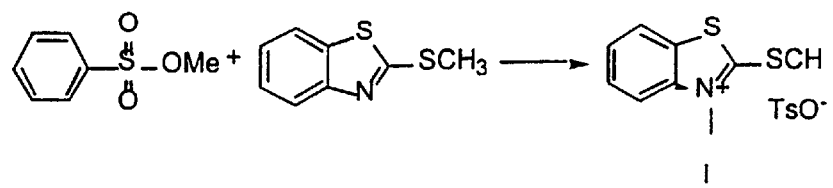
FIG. 14 illustrates the synthesis of BO-2-O.
Figure 14:
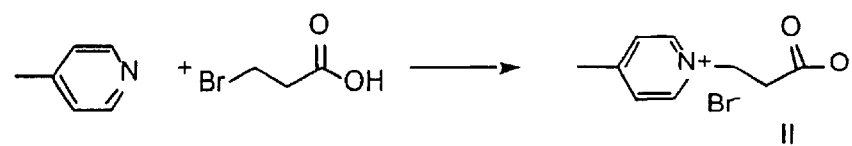
Figure 14:
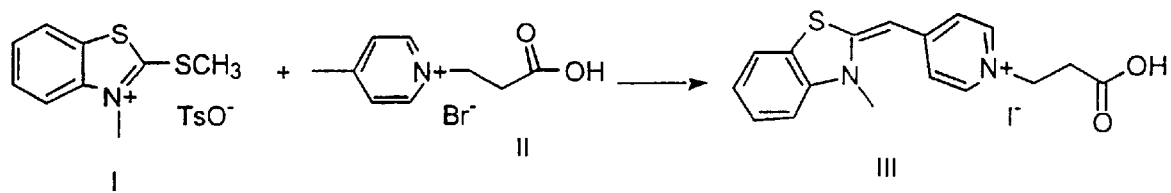

The synthesis was made in three steps p-toluene methyl sulphonate (35 g, 18.8 mmol) and 2-methylthiobenzothiazole (2.5 g, 14.0 mmol) was refluxed for 5 hours. The product (I) was re-crystallized in methanol/acetone (FIG. 14a).

Yield: 4.8 g, 13.1 mmol, 94%.

4-picoline (3.7 g, 40 mmol) and 3-bromopropionic acid (6.1 g, 40 mmol) was refluxed for 5 hours. The product (II) was re-crystallized in methanol/acetone (FIG. 14b).

Yield: 6.9 g, 28 mmol, 70%.

N-carboxyethyl-4-[(3-methyl-2(3H)-benzothiazolyliden) methyl pyridinium iodide was synthesized by condensation (overnight at room temperature) of I (1.8 g, 5 mmol) and II (1.2 g, 5 mmol) in the presence of $Et_3N$ (2.0 g, 20 mmol) in $CH_2Cl_2$ (10 ml). The product was precipitated with 30% KI(aq) (15 ml), filtered and re-crystallized in methanol/water.

Yield: 0.70 g, 2.1 mmol, 43%.

Example 6

Solid Phase Synthesis, Cleavage and Purification of Probe PP15-TGT-TO 20 mg Resin with a PNA substitution level of 0.15 mmol/g was swelled in DCM over night. The PNA sequence was Re-Lys-Lys-ATCAACACTGCATG-NH-Boc (SEQ ID NO:11), where 'Re' is the resin and Boc is the amino end protection group t-butyloxycarbonyl. The solid phase synthesis was performed on a glass funnel equipped with water suction and nitrogen stirring. Portions of washing and reagent solutions were 1 ml, and in the case of the coupling step was 0.3 ml. Boc was removed by adding 5% m-cresol in trifluoroaceticacid (TFA) and stirring for four min. This procedure was performed three times, where after the resin was washed with three portions of DCM:DMF (1:1) followed by two washes with pyridine. Free amino groups were detected by the Kaiser test. The PNA monomer Boc-thymine (9.8 mg, $18*10^{-6}$ mmol) was dissolved in 0.3 ml 2-(1H-Benzotriazole-1-yl)-1,1,3,3-tetramethyl uronium hexafluorophosphate (HBTU, 0.15 mM, $18*10^{-6}$ mol) in DMF. Diisopropylethylamine, DIEA (6.3 μl, $3.4*10^{-5}$ mol) was added after about 1 minute and the mixture was transferred to the resin and coupling reaction was allowed to proceed for 30 min. The Kaiser test showed no free amino groups at the end of the reaction. Unreacted monomer was filtered off and the resin was washed twice with DMF. Capping of any remaining amino groups was done by acetic anhydride and colidin in DMF (1:1:8) for two min. The resin was then washed three times with DMF and stirred with 5% piperidine in DMF for four min. Finally the resin was washed three times with DCM:DMF (1:1) and three times with DCM.

TO-5-O ($R_1$=$CH_2CH_2CH_2CH_2CH_2COOH$, 9.6 mg, $18*10^{-6}$ mol) was then coupled to the Re-Lys-Lys-ATCAACACTGCATGT-NH-Boc (SEQ ID NO:12) in the same way as the thymine, except that the coupling reaction was allowed to proceed for 45 min. The resin beads turned red during the reaction and the Kaiser test showed no free amino groups.

The dry resin was placed in an Eppendorf tube filter tube and washed with TFA (0.25 ml). Lys-Lys-ATCAACACTGCATGT-TO was cleaved from the resin and deprotected by addition of trifluoromethylsulfonicacid (TFMSA): TFA: m-cresol: thioanisole (2:6:1:1, 0.25 ml) for one hour. The mixture was then removed from the resin by centrifugation at 6000 rpm and transferred to a test-tube. The cleavage was repeated once and the resin was finally washed with TFA (0.25 ml). Half of the solvent was evaporated from the combined cleavage fractions with a flow of nitrogen. Ice cold diethylether (5 ml) was then added to the test-tube and white crystals precipitated. The tube was centrifuged at 6000 rpm and the supernatant removed. The probe (PP15-TGT-TO) was washed with four portions of ether and finally dissolved in 0.2 ml of water. Upon addition of water the probe turned red.

Figure 15:
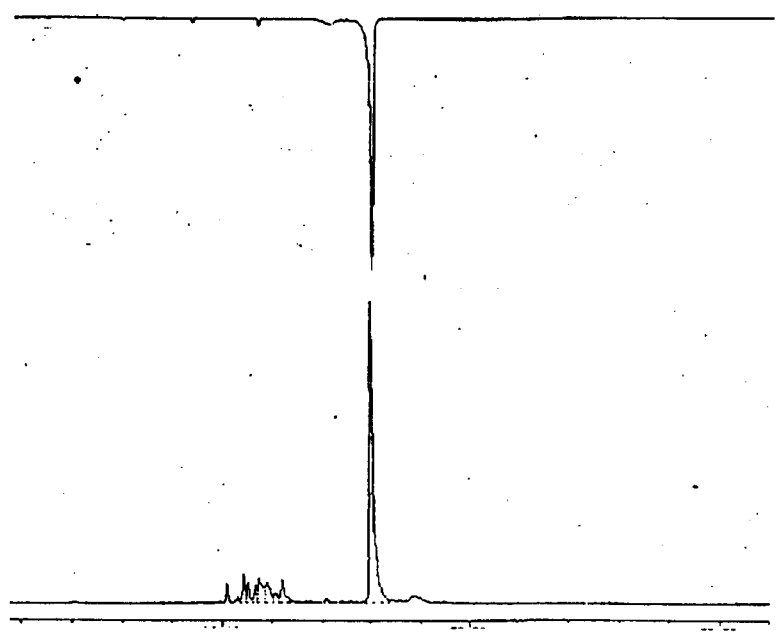
FIG. 15 A) illustrates the HPLC of solid-phase synthesized probe PP15TGT-TO B)
Figure 15:
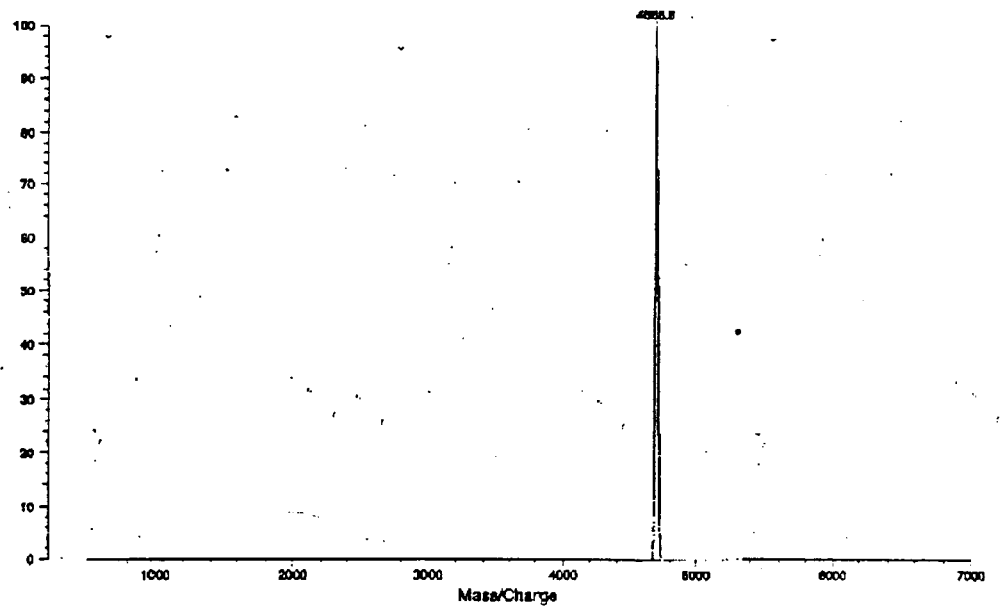

The probe was purified by reversed phase HPLC as described in Example 4 and characterized by MALDI-TOF MS (FIG. 15).

Example 7

Solid Phase Synthesis, Cleavage and Purification of Probe PP16-GTC-10c (probe with stiff linker)

20 mg resin with a PNA substitution level of 0.15 mmol/g was swelled in THF for three hours and then washed with DCM. The PNA sequence was Re-Lys-Lys-ATCAACACTGCATGT-NH-Boc (SEQ ID NO:12), to which first a cytosine was coupled as described in Example 6. In the next step a stiff linker was coupled as follows.

Boc-protected N-carboxymethylpiperazine (3.3 mg, $13.5×10^{-6}$ mol) was dissolved in DMF (0.5 ml) and HBTU (5.1 mg, $13.5×10^{-6}$ mol) and DIEA (4.8 μl, $2.75×10^{-5}$ mol)

were added. This mixture was then added to the amino end deprotected sequence. Coupling proceeded for 30 min, where after no free amino groups were detected by the Kaiser test. Unreacted monomer was filtered off and the resin was washed twice with DMF. Capping of any remaining amino groups was made using acetic anhydride and colidin in DMF (1:1:8) for two min. The resin was washed three times with DMF and then stirred with 5% piperidine in DMF for four min. The resin was finally washed three times with DCM:DMF (1:1) and three times with DCM. Boc was removed from the stiff linker as described in Example 6, and the Kaiser test detected the presence of secondary amine. TO-2-O ($R_1$=$CH_2CH_2COOH$, 6.6 mg, 13.5×10−6 mol) was dissolved in DMF (0.5 ml) and HBTU (5.1 mg, 13.5*10−6 mol) and DIEA (4.8 µl, 2.75*10−5 mol) were added. This mixture was then added to the resin. Coupling proceeded for 45 min and the resin turned red. Capping and washing were performed as in Example 6. The probe was then cleaved and deprotected as in Example 6.

The probe (PP16-GTC-TOc) was purified by reversed phase HPLC as described in Example 4 and characterized by MALDI-TOF MS.

Figure 8:
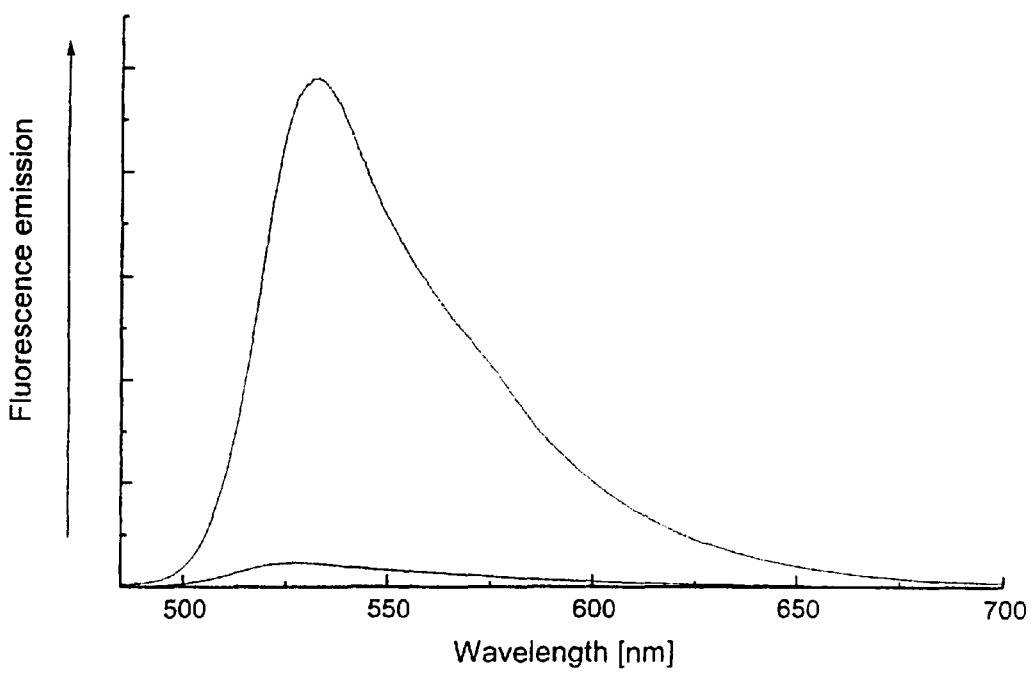
FIG. 8 illustrates the increase in fluorescence intensity upon hybridization of probe according to the design in FIG. 3A. Hybridization of the probe PP10-CTT-TO to ssDNA. (a) Fluorescence emission spectra and (b) fluorescence intensities of free probe, probe in presence of 5-fold excess of non-complementary ssDNA, and probe in presence of TS.
Figure 8:
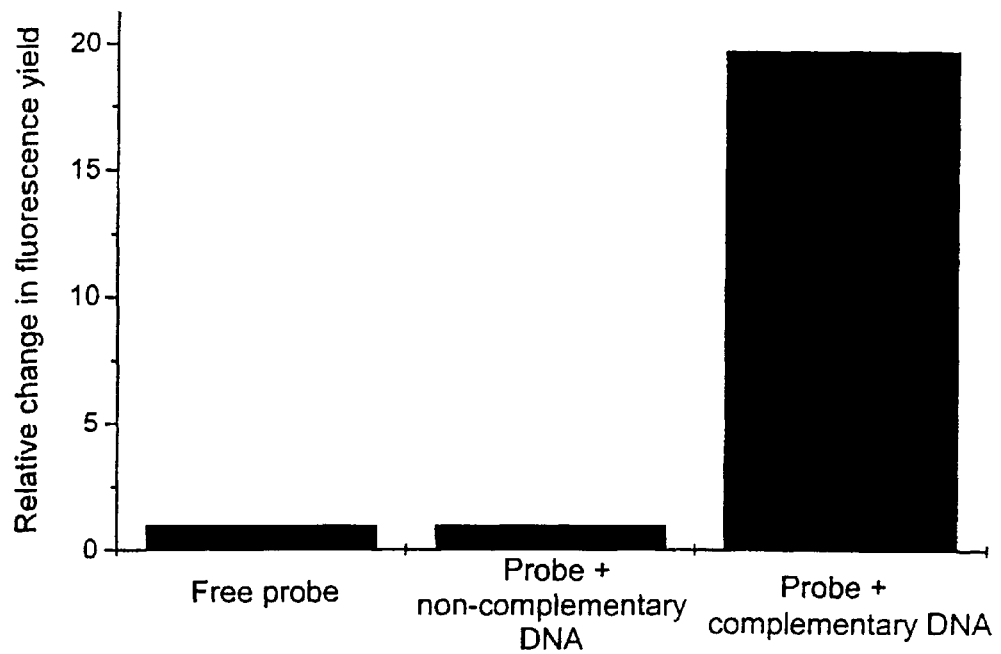

Example 8
Probing of ssDNA by Probe PP10-CTT-TO Using the Design Outlined in FIG. 3A First the background luminescence of the probe PP10-CTT-TO was measured. Then excess of non- complementary ssDNA (5'-TCCTTCATTCGCTTC-3') (SEQ ID NO: 13) was added, which did not affect the luminescence. Then ssDNA containing TS (5'-AGCGGTCGACAGAAGAAGAAAA-3') (SEQ ID NO:14) was added. This resulted in an instantaneous increase in luminescence (FIG. 8). The samples contained 1.4 µM probe, 5 mM borate buffer (pH 8.5) and 50 mM NaCl. Probing temperature was 50° C.

Figure 10:
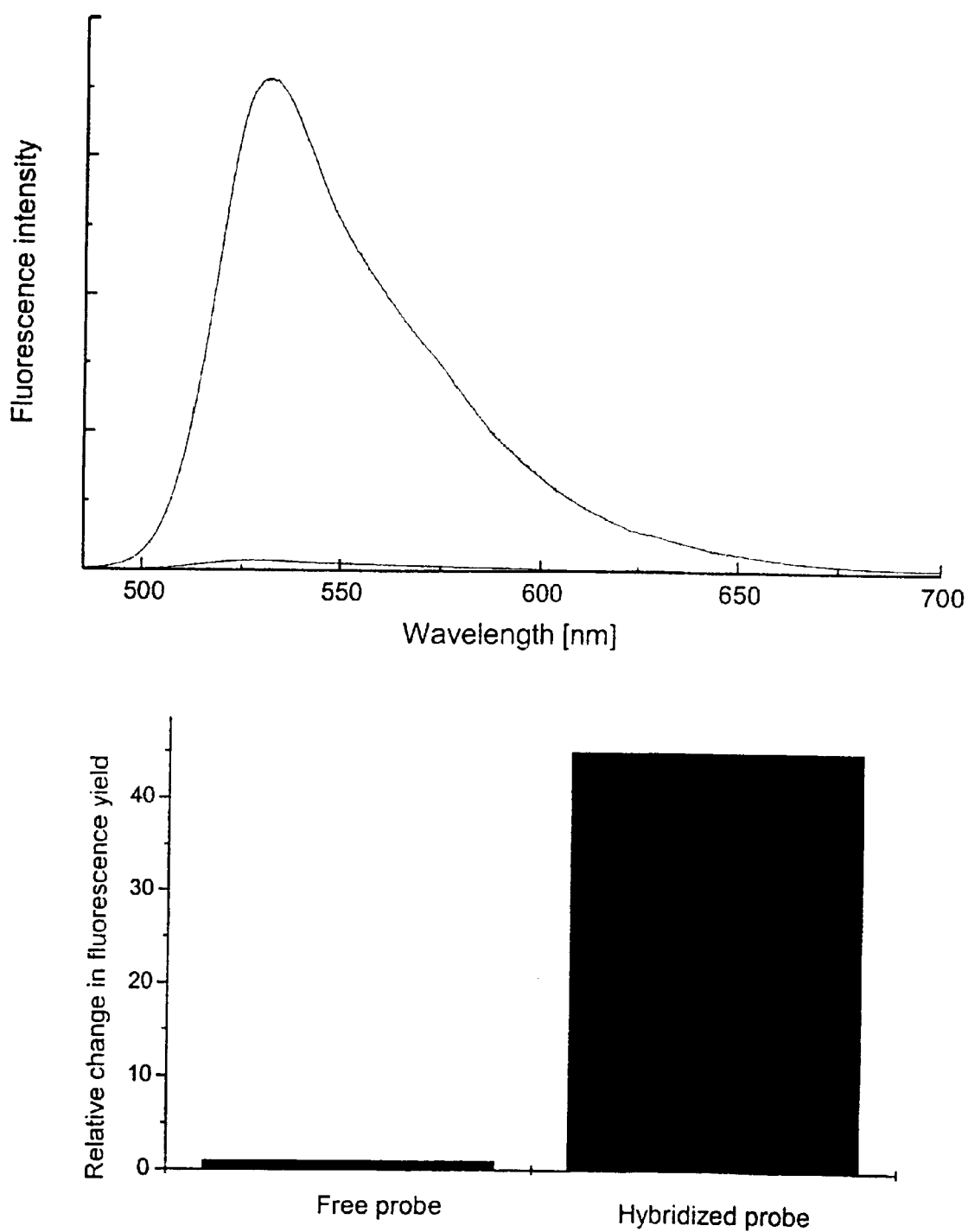
FIG. 10 illustrates the increases in probe fluorescence upon hybridization to TS according to the design in FIG. 6.

Example 9
Probing of ssDNA by Probe PP10-CTT-TO Using the Design Outlined in FIG. 6 ssDNA with the sequence 5'-AGCGGTCGACAGAAGAAGAAAA-3' was added to a sample containing the probe PP10-CTT-TO and the oligomer 5'-GTCGACCGCT-3', which are complementary to two close lying parts of the ssDNA. This resulted in a 45-fold increase in fluorescence (FIG. 10). The experiment was performed at 50° C. in 5 mM borate buffer (pH 8.5) at an ionic strength of 500 mM.

Figure 11:
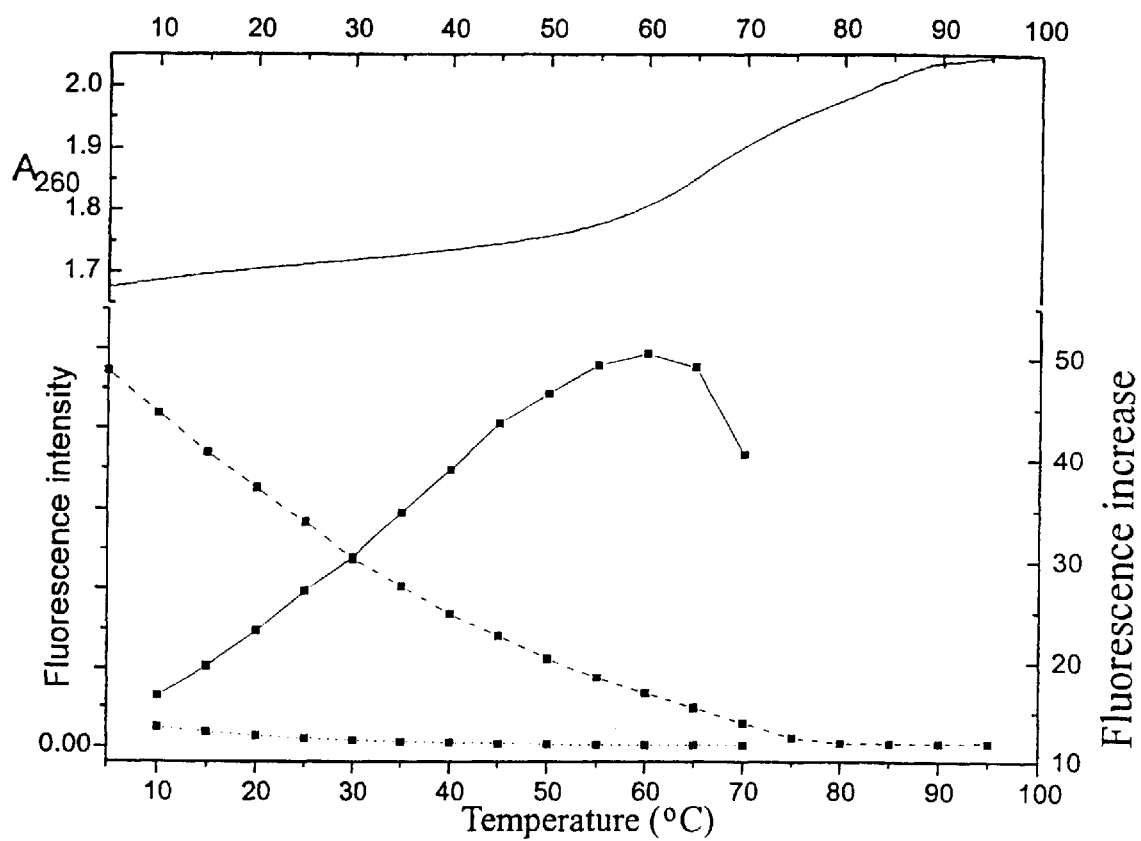
FIG. 11 illustrates the characterization of hybridized complex according to the desion in FIG. 6. Top solid line (no symbols): absorption at 260 nm as a function of temperature. Dashed line with symbols is the fluorescence of the hybridized probe. Dotted line with symbols is the background fluorescence of the free probe. Solid line with symbols is the ratio between the fluorescence of the hybridized probe and the fluorescence of the free probe (indicated by the right scale).

The probing mixture is further characterized in FIG. 11. From the absorption at 260 nm, measured as function of temperature, shows that the oligomer dissociates at about 65° C., as reflected by the first inflection point, and the PNA-based probe at about 85° C., as indicated by the second inflection point. This difference reflects the higher stability of PNA:NA hybrids compared to dsNA.

The fluorescence of both free and hybridized probe decreases with temperature. The former is probably due to reduced degree of residual back binding at higher temperature, while the latter is due to increased thermal fluctuations of the bases in the NA duplex, which allows for internal flexibility in RG and hence lower fluorescence. The enhancement in fluorescence upon hybridization is the ratio between these signals, and is maximal at about 62° C.

The fluorescence of the hybridized probe drops to background level at about 75° C., which is below the melting temperature of the PNA:NA duplex, but at a temperature where essentially no oligomer is bound. This supports the hypothesis that the dye in the hybridized state is bound to the NA:NA duplex region (Example 6).

Example 10
Construction of a Protein-RG Probe

A probe was constructed of the restriction enzyme EcoRI, which specifically recognizes the sequence 5'-GAATTC-3'/3'-CTTAAG-5' in dsNA, and BO. 200 nmol of BO succinimidyl ester, dissolved in DMSO, was added to 100 nmol EcoRI (from Life Technology) in 1 ml 20 nM phosphate buffer at pH 8.0. The BO solution was added gradually under stirring to avoid protein denaturation by the DMSO. The mixture was then agitated in the dark at 4° C. for 15 hour, and the probe was finally separated from free dye using a 10 K microconcentrator at 4° C. Fluorescence spectra of the free EcoRI probe, the probe in presence of dsDNA containing the EcoRI recognition site, and dsDNA lacking this site, here the DNA polymer poly(dAdT):poly(dAdT), are shown in FIG. 16. It is seen that the EcoRI probe specifically recognizes the TS-containing dsDNA. As a reference the fluorescence spectra of the free dye in the presence of the same DNAs is shown.

Example 11
Fluorescence Enhancement of SRE-RG Probes

| Code | Conditions | Mode | Increase in fluorescence upon hybridization |
|---|---|---|---|
| | NAA-based probes | | |
| PP10-CTT-TO | 5 mM boric buffer pH 8.5, 500 mM NaCl, 50° C. | 6 | 45 |
| PP10-CTT-TO | 5 mM boric buffer pH 8.5, 50 mM NaCl, 50° C. | 3A | 20 |
| PP10-CTT-TO | 5 mM boric buffer pH 8.5, 50 mM NaCl, 50° C. | 3A | 20 |
| PP10-CTT-BO | 10 mM boric buffer pH 8.5, 25° C. | 3A | 8 |
| PP10-CTT-BO | 10 mM boric buffer pH 8.5, 45° C. | 3A | 9 |
| PP5-GCT-TO | 10 mM boric buffer pH 8.5, 20° C. | 3A | 20 |
| PP11-TT-TO | 10 mM boric buffer pH 8.5, 45° C. | 3A | 10 |
| PP8-GCT-TO | 10 mM boric buffer pH 8.5, 45° C. | 3A | 35 |
| PP8-GCT-TO | 20 mM boric buffer, 500 mM NaCl, pH 8.5, 20° C. | 3A | 30 |
| PP8-GCT-TO | 10 mM phosphate buffer, pH 7.5, 25° C. | 3A | 27 |
| | Protein based probes | | |
| EcoRI | 10 mM phosphate buffer, pH 7.5, 25° C. | 3D | 50 |

Example 12
Determination of Quantum Yields

The fluorescence quantum yield of free and hybridized probe PP8-GCT-TO was determined relative to fluorescein. PP8-GCT-TO was dissolved in 10 mM phosphate buffer, pH 7.5, at a probe concentration of 0,8 µM. Absorption measurements were performed on a Varian Cary 4 and fluorescence measurements on a spex fluorolog t2. All measurements were made using the same 1 cm cell. The samples were excited at 470 nm and spectra were recorded between 480 and 700 nm, collecting five data points per nm. The fluorescence quantum yields ($\Phi_F$) were determined relative to the fluorescein dianion in 0,1 M NaOH (assuming a quantum yield of 0.93). The quantum yield were calculated from:

$$\Phi_F = \frac{\int_{-\infty}^{\infty} F_s(\upsilon) d\upsilon}{\int_{-\infty}^{\infty} F_f(\upsilon) d\upsilon} \cdot \frac{0.93 \, A_s^{\lambda ex}}{A_s^{\lambda ex}} \quad (1)$$

where F(v) is the fluorescence emission intensity at wavelength v, and $A^{\lambda ex}$ is the absorption at excitation wavelength. Hybridization was made with the ssDNA 5'-ATC GAC GAG AGA ATA TCA (SEQ ID NO: 15) in a 1:1 ratio. The results and summarized below.

| Sample | $\Phi_F$ | $\Phi_F(H)/\Phi_F(F)$* |
|---|---|---|
| Free PP8-GCT-TO at 25° C. | 0.0066 | — |
| PP8-GCT-TO mixed with equal amount of complementary ssDNA, 25° C. | 0.16 | 24 |
| Sample above heated to 80° C. for 5 min and then brought back to 25° C. | 0.18 | 27 |

*Increase in fluorescence quantum yield upon hybridization. Note that the increase in quantum yield is not necessarily identical to the increase in fluorescence intensity owing to differences in absorption between free and hybridized probe.

Example 13
Attenuation of the Background Signal

Figure 17:
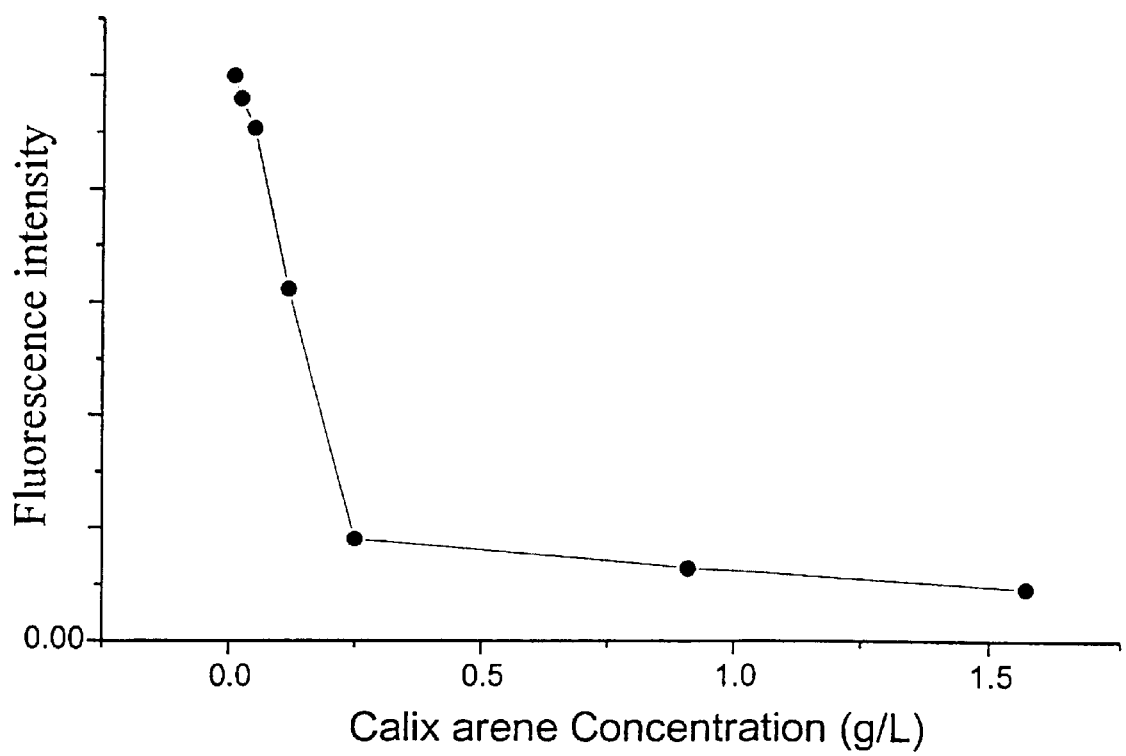
FIG. 17 illustrates the effect of complexing agent. Fluorescence of the free probe PP15-GAT-BO in presence of various concentrations of calixarene. The background fluorescence decreases almost 6-fold at modest additions of calixarene (0.25 g/L).

The background fluorescence signal from the probe PP15-GAT-BO is reduced by addition of calixarene (FIG. 17), which, most likely, sequesters RG from the SRE. The concentration of the PP15-GAT-BO probe was 1 $\mu$M, temperature was 15° C. 10 mM Tris buffer, pH 7.5, was used.

Example 14
Comparison of NAA-RG and NA-RG Probes

A PNA-TO (PP8-GCT-TO) and a NA-TO probe (PD8-GCT-TO) were synthesized with the same sequences and comparable linkers. Fluorescence was measured of the free probes and of the probes hybridized to NA containing TS at three temperatures (FIG. 18). In all cases is the fluorescence of the free PNA-based probe lower than of the NA-based probe, and the fluorescence of the hybridized PNA-based probe higher than that of the hybridized NA-based probe.

Example 15
Visual Detection

Figure 13:
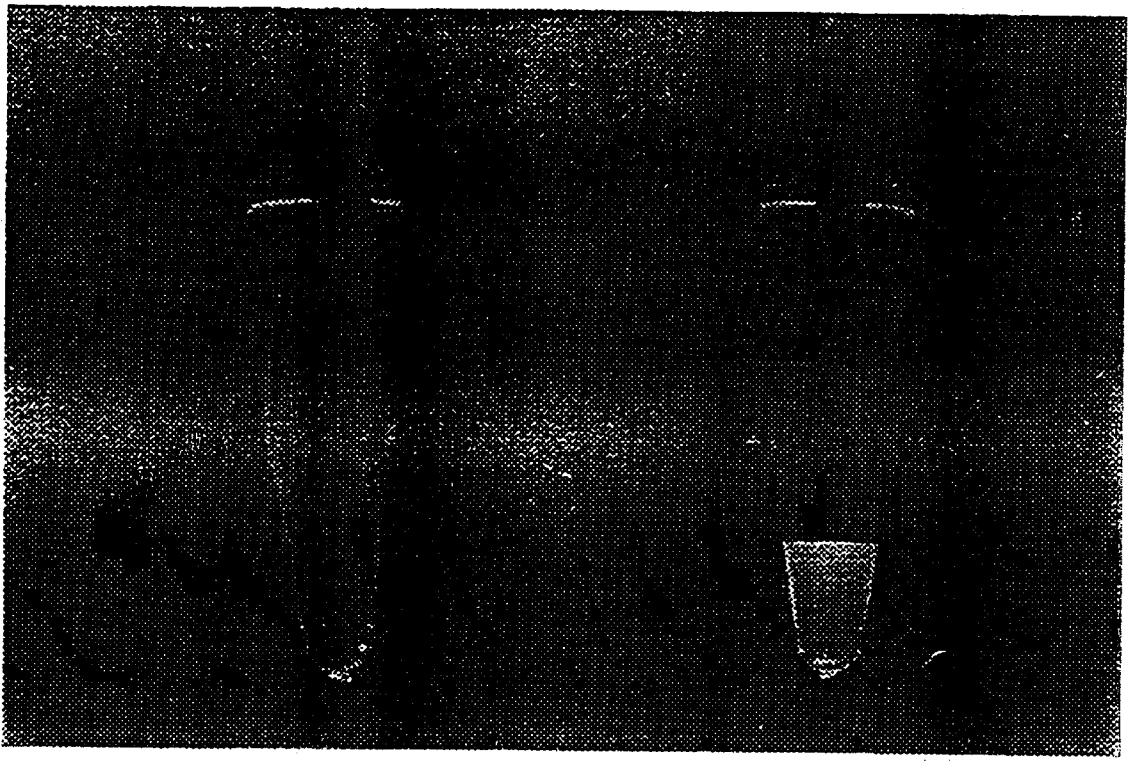
FIG. 13 illustrates the direct observation of hybridization. Photograph of samples containing probe PP10-CTT-TO in presence of non-complementary NS (left) and NS containing TS. The samples are illuminated from beneath using a UV generating lamp, and photographed by a standard camera. No filters used.

Direct observation of hybridization between probe and TS. FIG. 13 shows two polypropylene tubes illuminated from below with a broad pass UV lamp and photographed from the side (using an ASA 200 film, no filters). Both tubes contain 30 $\mu$l sample and 3.5×10$^{-10}$ mol probe. The left sample contains also a 5-fold excess of non-complementary NA, while the right luminous sample contains complementary NA. Same oligomers as in Example 12 were used. Conditions were 10 mM Borate buffer, pH 8.5, no salt, 30° C.

What is claimed is:

1. A probe for target nucleic acid sequences (TS) comprising a sequence recognizing element (SRE) which in its entirety sequence specifically binds to TS, and a reporter group(-s) (RG) covalently bound to said SRE and having an observable signal property, wherein the binding of said probe to a nucleic acid (NA) comprising said target sequence (TS) results in the observable signal property of said RG being altered in a manner that is distinguishable from the observable signal property of said RG in the absence of binding to said target sequence, wherein said SRE has a structure, at least in a portion adjacent to said RG, that suppresses any intramolecular interaction between the SRE and the RG that will affect the observable signal property, or said SRE has a base sequence, at least in a portion adjacent to said RG, that suppresses any intramolecular interaction between the SRE and the RG that will affect the observable signal property.

2. A probe for target nucleic acid sequences (TS) comprising a sequence recognizing element (SRE) which in its entirety sequence specifically binds to TS, and a reporter group(-s) (RG) covalently bound to said SRE and having an observable signal property, wherein the binding of said SRE to a nucleic acid (NA) comprising said target sequence (TS) results in the observable signal property of said RG being altered in a manner that is distinguishable from the observable signal property of said RG in the absence of binding to said target sequence, wherein said SRE has a structure, at least in a portion adjacent to said RG, that suppresses any intramolecular interaction between the SRE and the RG that will affect the observable signal property, or said SRE has a base sequence of mixed pyrimidines, at least in a portion adjacent to said RG, that suppresses any intramolecular interaction between the SRE and the RG that will affect the observable signal property.

3. Probe according to claim 1, wherein the SRE, at least in a portion adjacent to the RG, has a structure different from that of a natural nucleic acid.

4. Probe according to claim 1, wherein the SRE is selected from the group consisting of:

a synthetic deoxyribonucleic acid analogue (NAA), a sequence recognizing protein or peptide, a deoxyribonucleic acid analogue joined to a protein or a peptide, and an oligonucleotide joined to a protein or a peptide.

5. Probe according to claim 1, wherein the SRE is a nucleic acid (NA) comprising a nucleotide base or bases, at least in a portion adjacent to said RG, for which RG has a low affinity and/or interaction between said RG and said nucleotide base or bases minimally affects the observable signal property.

6. Probe according to claim 4, wherein the SRE is a NAA comprising a modified or replaced phosphodiester backbone or modified or replaced sugar moieties attached thereto, and a stereochemistry different from natural NA.

7. Probe according to claim 6, wherein the NAA has a neutral charge or a positive net charge that is no more than one charge per base.

8. Probe according to claims 6 or 7, wherein the NAA is peptide nucleic acid (PNA).

9. Probe according to claim 1, wherein the observable signal property is luminescence.

10. Probe according to claim 1, wherein the observable signal property of said RG increases in intensity upon binding of said SRE to said nucleic acid comprising said TS.

11. Probe according to claim 1, wherein the reporter group comprises the following characteristics:

a) an affinity for ssNA and/or dsNA between 0.1 and $10^3$ $M^{-1}$ ($-1<\log K<8$);

b) a quantum yield of luminescence in aqueous solution that is less than 0.05;

c) a quantum yield of luminescence when bound to NA that is larger than 0.01;

d) an increase in luminescence quantum yield upon binding to a NA that is at least 5-fold; and e) a maximum molar absorptivity of at least 1,000 $M^{-1}cm^{-1}$.

12. Probe according to claim 10, wherein the reporter group comprises aromatic moieties out of which at least two are joined by a covalent linkage that is in conjugation with an aromatic system.

13. Probe according to claim 1, wherein the reporter group is an asymmetric cyanine compound.

14. Probe according to claim 13, wherein the asymmetric cyanine compound has in its unbound form one out of the following chemical structures:

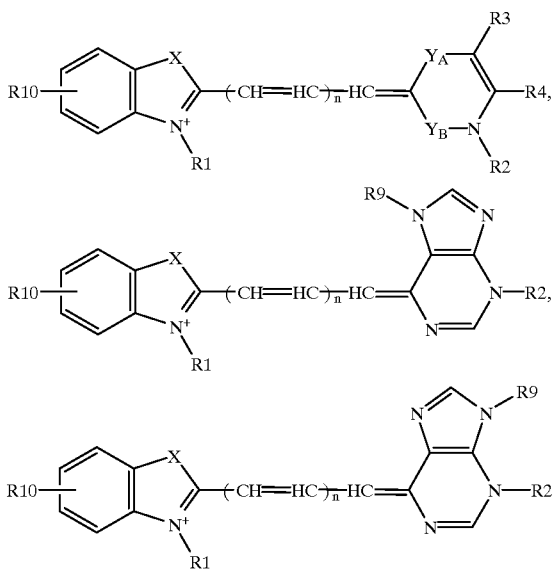

where R¹ is a hydrogen or to the nitrogen a non-conjugated alkyl group having at most 6 carbon atoms, which alkyl group may be substituted with polar residues selected from the group consisting of hydroxy, alkoxy, carboxy, and amino groups, where X is O, S, Se, $NR^5$, wherein $R^5$ is hydrogen or an alkyl group having at most 6 carbon atoms, or $CR^6R^7$, wherein R6 and $R^7$, independently from each other, are hydrogen or an alkyl group having at most 6 carbon atoms, where $R^2$, $R^3$, and $R^4$, of which two or three may be the same, are hydrogen, small alkyl groups, aryl residues, or in pair, $R^2$ and $R^4$, or $R^3$ and $R^4$, and in combination with two of the ring atoms, to which they are attached, constitute a 5- or 6-membered aromatic ring that may contain 0–2 hereto atoms or $NR^5$, wherein $R^5$ has the meaning as given above, where n is 0, 1 or 2 where Y is HC=CH, and A and B are both 0 or 1, with the proviso that when A is 1 B is 0, and vice versa;

where $R^9$ and $R^{10}$, independently, are hydrogen or to the nitrogen non-conjugated alkyl groups having at most 6 carbon atoms, which alkyl group may be substituted with polar residues selected from the group consisting of hydroxy, alkoxy, carboxy, and amino groups.

15. Probe according to claim 7, wherein the RG is positively charged.

16. Probe according to claim 1, wherein the SRE and the RG are linked to each other via a hydrocarbon chain containing one or more of:
a) stiff group,
b) hetero atoms,
c) polar groups,
d) charged groups, and
e) bulky groups.

17. Probe according to claim 1, wherein the linkage between the SRE and the RG has at least one positive charge.

18. Probe according to claim 13, wherein the SRE is an NAA or NA, and more than 50% of its bases are of the pyrimidine kind.

19. Probe according to claim 13, wherein there is a pyrimidine base in at least every second position.

20. Probe according to claim 13, wherein the bases at the end to which RG is attached, are two thymines, or a cytosine and a thymine.

21. Probe according to claim 13, wherein all bases are pyrimidines.

22. Process of attaching a compound having one of the following chemical structures:

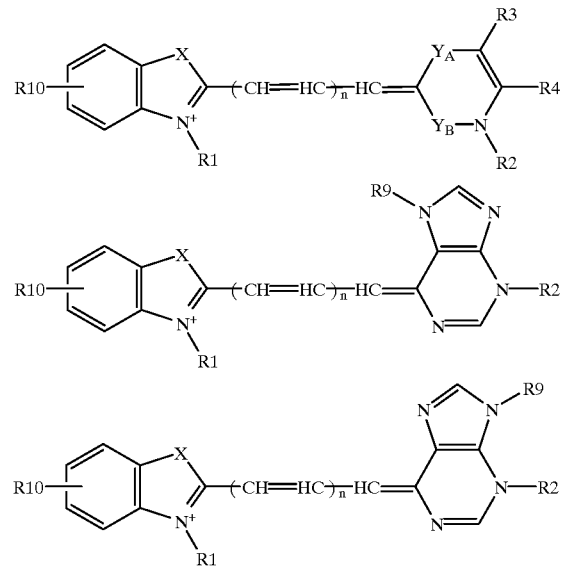

where R¹ is a hydrogen or to the nitrogen a non-conjugated alkyl group having at most 6 carbon atoms, which alkyl group may be substituted with polar residues selected from the group consisting of hydroxy, alkoxy, carboxy, and amino groups, where X is O, S, Se, $NR^5$, wherein $R^5$ is hydrogen or an alkyl group having at most 6 carbon atoms, or $CR^6R^7$, wherein $R^6$ and $R^7$, independently from each other, are hydrogen or an alkyl group having at most 6 carbon atoms, where $R^2$, $R^3$, and $R^4$, of which two or three may be the same, are hydrogen, small alkyl groups, aryl residues, or in pair, $R^2$ nd $R^4$, or $R^3$ and $R^4$, and in combination with two of the ring atoms, to which they are attached, constitute a 5- or 6-membered aromatic ring that may contain 0–2 hereto atoms or $NR^5$, wherein $R^5$ has the meaning as given above, where n is 0, 1 or 2 where Y is HC=CH, and A and B are both 0 or 1, with the proviso that when A is 1 B is 0, and vice versa;

where $R^9$ and $R^{10}$, independently, are hydrogen or to the nitrogen non-conjugated alkyl groups having at most 6 carbon atoms, which alkyl group may be substituted with polar residues selected from the group consisting of hydroxy, alkoxy, carboxy, and amino groups, and where $R^1$, $R^2$, $R^3$, $R^4$, $R^5$, $R^6$, $R^7$, $R^9$, $R^{10}$ are hydrocarbon chain that may be substituted with polar residues, and contain stiff groups, charged groups, or bulky groups, and one of said groups comprises an isothiocyanine, imidyl, sulfonyl chloride or carbonyl group being separated by at least one $sp^3$-hybridized carbon atom from the aromatic system, to an amino group in a SRE to form a probe according to claim 1, comprising
attaching said compound to said amino group by standard peptidizing synthesis.

23. A method for detecting a target sequence (TS) in a sample comprising dsNA, without prior separation of the dsNA strands, comprising the steps of:

adding a probe in accordance with claim 1 comprising an SRE and a RG to said sample;

allowing hybridization of said probe and said target sequence (TS) to occur; and detecting the observable signal property of said RG that is altered in a manner that is distinguishable from the observable signal property of said RG in the absence of binding to said target sequence (TS).

24. A method for detecting a target sequence (TS) in a sample comprising dsNA, to one of the dsNA strands at conditions wherein the dsNA is unstable, comprising the steps of:

adding a probe in accordance with claim 1 comprising an SRE and a RG to a said sample;

allowing hybridization of said probe and said target sequence (TS) to occur; and detecting the observable signal property of said RG that is altered in a manner that is distinguishable from the observable signal property of said RG in the absence of binding to said target sequence (TS).

25. A method for detecting or quantifying a specific NA in a sample containing active enzymes comprising the steps of:

adding a probe in accordance with claim 6 comprising an SRE, wherein said SRE is an NAA that is resistant to degradation from said active enzymes, and a RG to said sample comprising said specific NA;

allowing hybridization of said probe and said specific NA to occur; and detecting the observable signal property of said RG that is altered in a manner that is distinguishable from the observable signal property of said RG in the absence of binding to said specific NA.

26. A method for quantifying a specific NA in real time, in a sample comprising NA modifying, NA degrading, and NA synthesizing enzymes, comprising the steps of:

adding a probe in accordance with claim 6 comprising an SRE, wherein said SRE is an NAA that is resistant to modification or degradation from said enzymes, and a RG to said sample comprising said specific NA;

allowing hybridization of said probe and said specific NA to occur; and detecting the observable signal property of said RG that is altered in a manner that is distinguishable from the observable signal property of said RG in the absence of binding to said specific NA.

27. A method for detecting a target sequence (TS) in a sample comprising ssNA comprising the steps of:

providing a probe in accordance with claim 1 comprising an SRE and a RG;

providing an oligomer that binds to a portion of the ssNA located adjacent to said TS;

adding said probe and said oligomer to said sample;

allowing hybridization of said probe and said target sequence (TS) and hybridization of said oliogomer and said portion of the ssNA located adjacent to said TS to occur, wherein said RG binds to a duplex formed by the hybridization of said oligomer and said portion of the ssNA located adjacent to said TS; and detecting the observable signal property of said RG that is altered in a manner that is distinguishable from the observable signal property of said RG in the absence of binding to said target sequence (TS).

28. A method for detecting or quantifying a NA comprising the steps of:

immobilizing a probe in accordance with claim 1, comprising an SRE and a RG to a substrate;

adding a sample comprising said NA to said substrate;

allowing hybridization of said probe and said NA to occur; and detecting the observable signal property of said RG that is altered in a manner that is distinguishable from the observable signal property of said RG in the absence of binding to said NA.

29. Probe according to claim 1 containing more than one RG, which RGs may be identical, and whose individual or combined signal properties are altered.

30. Probe according to claim 1 or claim 19, containing at least one RG linked to either one or more out of a) nucleotide bases b) back-bone atoms, c) sugar atoms and/or atoms.

31. A probe for target nucleic acid sequences (TS) comprising a sequence recognizing element (SRE) which in its entirety sequence specifically binds to TS, and a reporter group(-s) (RG) covalently bound to said SRE and having an observable signal property, wherein the binding of said probe to a nucleic acid (NA) comprising said target sequence (TS) results in the observable signal property of said RG being altered in a manner that is distinguishable from the observable signal property of said RG in the absence of binding to said target sequence, wherein said SRE has a structure, at least in a portion adjacent to said RG, that suppresses any intramolecular interaction between the SRE and the RG that will affect the observable signal property, or said SRE has a base sequence, at least in a portion adjacent to said RG, that suppresses any intramolecular interaction between the SRE and the RG that will affect the observable signal property, and wherein said reporter group is a compound with the chemical structure:

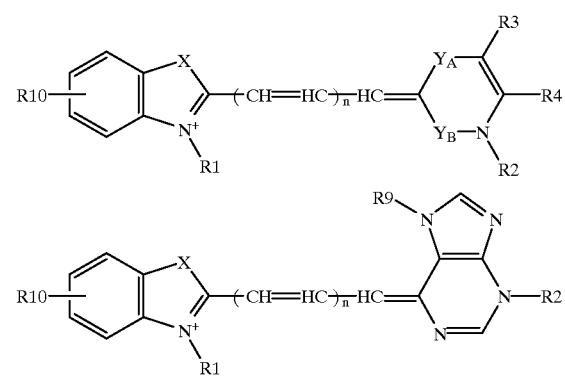

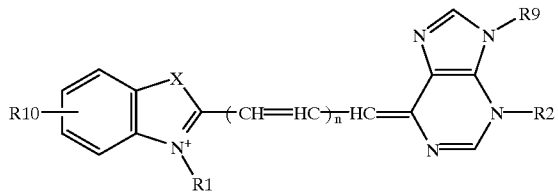

where R¹ is a hydrogen or to the nitrogen a non-conjugated alkyl group having at most 6 carbon atoms, which alkyl group may be substituted with polar residues selected from the group consisting of hydroxy, alkoxy, carboxy, and amino groups, where X is O, S, Se, NR⁵, wherein R⁵ is hydrogen or an alkyl group having at most 6 carbon atoms, or CR⁶R⁷, wherein R⁶ and R⁷, independently from each other, are hydrogen or an alkyl group having at most 6 carbon atoms, where R², R³, and R⁴, of which two or three may be the same, are hydrogen, small alkyl groups, aryl residues, or in pair, R² and R⁴, or R³ and R⁴, and in combination with two of the ring atoms, to which they are attached, constitute a 5- or 6-membered aromatic ring that may contain 0–2 hereto atoms or NR⁵, wherein R⁵ has the meaning as given above, where n is 0, 1 or 2 where Y is HC=CH, and A and B are both 0 or 1, with the proviso that when A is 1, B is 0, and vice versa;

where R⁹ and R¹⁰, independently, are hydrogen or to the nitrogen non-conjugated alkyl groups having, which alkyl group may be substituted as specified below, and R¹, R², R³, R⁴, R⁵, R⁶, R⁷, R⁹, R¹⁰ are hydrocarbon chain that may have polar residues, such as hydroxyl groups, alkoxy groups, carboxyl groups, and amino groups, and one of R¹, R², R³, R⁴, R⁵, R⁶, R⁷, R⁹, R¹⁰ has a carboxylic acid group that is separated by at least one sp3-hybridized carbon atom from the aromatic system.

32. Compound according to claim 31, wherein the carboxylic acid group is situated on a hydrocarbon side chain that is attached to a ring nitrogen.

33. A method for localizing a segment in a chromosome or part of a chromosome, comprising the steps of:
adding a probe in accordance with claim 1 or 29 comprising an SRE and a RG to a sample comprising said chromosome part or segment;
allowing hybridization of said probe and said chromosome part or segment to occur thus forming a hybrid; and
detecting the observable signal property of said RG that is altered in a manner that is distinguishable from the observable signal property of said RG in the absence of binding to said chromosome part or segment by direct observation of the hybrid through fluorescence microscopy.

34. Probe according to claim 1, wherein said RG binds to a single-stranded nucleic acid adjacent to said TS.

35. Probe according to claim 1, wherein said RG binds to a duplex nucleic acid formed by the binding of said SRE to said TS.

36. Probe according to claim 35, wherein the observable signal property of said RG bound to said duplex nucleic acid is enhanced when compared to the observable signal property of said RG in the absence of binding to said duplex nucleic acid.

37. Probe according to claim 7, wherein the NAA has a neutral net charge or a positive net charge that is no more than one charge per three bases.

38. Probe according to claim 11, wherein the quantum yield of luminescence in aqueous solution is less than 0.01.

39. Probe according to claim 11, wherein the quantum yield of luminescence in aqueous solution is less than 0.001.

40. Probe according to claim 11, wherein the quantum yield of luminescence when bound to NA is larger than 0.1.

41. Probe according to claim 11, wherein the quantum yield of luminescence when bound to NA is larger than 0.25.

42. Probe according to claim 11, wherein the increase in luminescence quantum yield upon binding to a NA is at least 50-fold.

43. Probe according to claim 11, wherein the increase in luminescence quantum yield upon binding to a NA is at least 500-fold.

44. Probe according to claim 11, wherein the maximum molar absorptivity is at least 10,000 $M^{-1}cm^{-1}$.

45. Probe according to claim 11, wherein the maximum molar absorptivity is at least 50,000 $M^{-1}cm^{-1}$.

46. Probe according to claim 14, wherein said hetero atoms are oxygen or sulfur.

47. Process according to claim 22, wherein said hetero atoms are oxygen or sulfur.

48. Compounds according to claim 31, wherein said hetero atoms are oxygen or sulfur.

49. Probe according to claim 16, wherein said stiff group is a double or triple bond.

50. Compound according to claim 32, wherein said compound is TO or BO.

51. Compound according to claim 32, wherein said hydrocarbon side chain is R¹, R² or R⁹.

* * * * *

SEQUENCE LISTING

<160> NUMBER OF SEQ ID NOS: 16

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: partial PNA
      sequence codes: PP10-CTT-TO and  PP10-CTT-BO and
      NA-based probe code: PD10-CTT-TO

<400> SEQUENCE: 1
ttcttctttt                                                            10

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Partial PNA
      sequence codes: PP11-TT-TO and NA-based probe
      code: PD11-CTT-TO

<400> SEQUENCE: 2
ttctcgtcga t                                                          11

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Partial PNA
      sequence codes: PP8-GCT-TO and NA-based probe
      code: PD8-GCT-TO

```
<400> SEQUENCE: 3 tcgtcgat                                                                   8

<210> SEQ ID NO 4
<211> LENGTH: 5
<212> TYPE: DNA
<213> ORGANISM: Artificial Sequence
<220> FEATURE:
<223> OTHER INFORMATION: Description of Artificial Sequence:Partial PNA
      sequence code: PP5-GCT-TO

<400> SEQUENCE: 4 tcgat                                                                      5

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:Partial PNA
      sequence codes: PP15-TGT-TO and PP15--TGT-BO

<400> SEQUENCE: 5
tgtacgtcac aacta                                                          15

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence:Partial PNA
      sequence codes: PP16-GTC-TOa, PP16-GTC-TOb and
      PP16-GTC-TOc

<400> SEQUENCE: 6
ctgtacgtca caacta                                                         16

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:Partial PNA
      sequence code: PP15-GAT-BO

<400> SEQUENCE: 7
tagttgtgac gtaca                                                          15

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence:NA-based
      probe code: PD11-CAT-TO

<400> SEQUENCE: 8
tactcgtcga t                                                              11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence:NA-based
      probe codes: PD11-CTC-TO and PD11-CCT-TO
```

```
<400> SEQUENCE: 9
ctctcgtcga t                                                              11

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence:Partial PNA
      sequence

<400> SEQUENCE: 10
ttttcttctt                                                                10

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence:Partial PNA
      sequence

<400> SEQUENCE: 11
atcaacactg catg                                                           14

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence:Partial PNA
      sequence

<400> SEQUENCE: 12
atcaacactg catgt                                                          15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:Synthetic
      non-complimentary ssDNA

<400> SEQUENCE: 13
tccttcattc gcttc                                                          15

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:ssDNA
      containing TS

<400> SEQUENCE: 14
agcggtcgac agaagaagaa aa                                                  22

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence:oligomer
      complimentary to two close lying parts of ssDNA

<400> SEQUENCE: 15
```

```
gtcgaccgct                                                          10

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:ssDNA

<400> SEQUENCE: 16
atcgacgaga gaatatca                                                 18
```